US008852552B2

(12) United States Patent
Strom et al.

(10) Patent No.: US 8,852,552 B2
(45) Date of Patent: Oct. 7, 2014

(54) AGENTS AND METHODS FOR VISUALIZING ANALYTES

(75) Inventors: Hans Eric Peter Strom, Trosa (SE); Samuel Par Simon Svensson, Ljungsbro (SE)

(73) Assignee: Biopercept AB, Hjärup (SE)

( * ) Notice: Subject to any disclaimer, the term of this patent is extended or adjusted under 35 U.S.C. 154(b) by 0 days.

(21) Appl. No.: 13/885,393

(22) PCT Filed: Nov. 15, 2011

(86) PCT No.: PCT/EP2011/070172
§ 371 (c)(1),
(2), (4) Date: May 14, 2013

(87) PCT Pub. No.: WO2012/066006
PCT Pub. Date: May 24, 2012

(65) Prior Publication Data
US 2013/0323168 A1    Dec. 5, 2013

(30) Foreign Application Priority Data
Nov. 15, 2010   (GB) .................................. 1019303.5

(51) Int. Cl.
*G01N 33/60* (2006.01)
*C07F 9/80* (2006.01)
*C07F 9/655* (2006.01)
*A61K 49/10* (2006.01)
*C07F 9/70* (2006.01)
*A61K 51/04* (2006.01)
*A61K 51/08* (2006.01)

(52) U.S. Cl.
CPC ............. *A61K 51/0472* (2013.01); *C07F 9/80* (2013.01); *G01N 33/60* (2013.01); *C07F 9/65522* (2013.01); *A61K 49/10* (2013.01); *C07F 9/706* (2013.01); *A61K 51/0421* (2013.01); *A61K 51/088* (2013.01); *A61K 51/086* (2013.01)
USPC .......................... 424/1.49; 549/207; 424/1.89

(58) Field of Classification Search
CPC combination set(s) only.
See application file for complete search history.

(56) References Cited

U.S. PATENT DOCUMENTS

| 5,932,474 | A | 8/1999 | Tsien et al. | |
|---|---|---|---|---|
| 6,008,378 | A | 12/1999 | Tsien et al. | |
| 6,054,271 | A * | 4/2000 | Tsien et al. | 435/6.16 |
| 6,933,384 | B2 * | 8/2005 | Tsien et al. | 544/104 |
| 2003/0083373 | A1 | 5/2003 | Tsien et al. | |

FOREIGN PATENT DOCUMENTS

| GB | 1221597 A | 2/1971 |
|---|---|---|
| WO | 9921013 A1 | 4/1999 |
| WO | 03107010 A1 | 12/2003 |
| WO | 2005040197 A1 | 5/2005 |
| WO | 2005054427 A3 | 6/2005 |
| WO | 2006001925 A1 | 1/2006 |
| WO | 2007020400 A1 | 2/2007 |
| WO | 2007144077 A2 | 12/2007 |
| WO | 2008003954 A1 | 1/2008 |

OTHER PUBLICATIONS

Spagnuolo, C.C.; Massad, W.; Miskoski, S.; Menendez, G.O.; Garcia, N.A.; Jares-Erijman, E.A. "Photostability and Spectral Properties of Fluorinated Fluoresceins and their Biarsenical Derivatives: A Combined Experimental and Theoretical Study" Photochemistry and Photobiology 2009, 85, 1082-1088.*

Shevchenko, V.P.; Nagaev, I.Y.; Myasoedov, N.F. "Use of Methyl p-Toluenesulfonate Labeled with Hydrogen Isotopes as a Donor of Methyl Group" Radiochemistry 2009, 51, 2, 178-182.*

Adams, S.R.; Campbell, R.E.; Gross, L.A.; Martin, B.R.; Walkup, G.K.; Yao, Y.; Llopis, J;, Tsien, R.Y. "New Biarsenical Ligands and Tetracysteine Motifs for Protein Labeling in Vitro and in Vivo: Synthesis and Biological Applications" JACS 2002, 124, 6063-6076.*

Adams, et al., "New Biarsenical Ligands and Tetracysteine Motifs for Protein Labeling in Vitro and in Vivo: Synthesis and Biological Applications", J. Am. Chem. Soc., 2002, vol. 124, pp. 6063-6076.

Adams, et al., "Preparation of the membrane-permeant biarsenicals, FlAsH-EDT2 and ReAsH-EDT2 for fluorescent labeling of tetracysteine-tagged proteins", Nat. Protoc., 2008, vol. 3(9), pp. 1527-1534.

Ali, et al., "Synthesis of Radiopharmaceuticals via Organotin Intermediates", Synthesis, Apr. 1996, pp. 423-445.

Antoni, et al., "C: Labeling Chemistry and Labeling Compounds", Handbook of Nuclear Chemistry, (Vertes, A., Nagy, S., Klenscar Z., Eds.), 2003, vol. 4, pp. 119-165.

Cheng, et al., "Small-Animal PET of Melanocortin 1 Receptor Expression Using a 18F-Labeled α-Melanocyte-Stimulating Hormone Analog", J. Nucl. Med., 2007, vol. 48, pp. 987-994.

Genin, et al., "CrAsH-Quantum Dot Nanohybrids for Smart Targeting of Proteins", J. Am. Chem. Soc., 2008, vol. 130, pp. 8596-8597.

(Continued)

*Primary Examiner* — Sean Basquill
*Assistant Examiner* — Andrew S Rosenthal
(74) *Attorney, Agent, or Firm* — VLP Law Group LLP; Richard G. A. Bone

(57) ABSTRACT

Provided herein are novel compounds based on xanthene, for example biarsenical compounds, which are useful as molecular probes. The compounds contain at least one isotope atom, such as a radioisotope atom. Methods for visualizing tetracysteine-tagged analyte molecules such as proteins using said compounds, methods for synthesizing said compounds, and methods for treating cancer or other hyperproliferative disorders using said compounds are also provided.

35 Claims, 6 Drawing Sheets

(56) References Cited

OTHER PUBLICATIONS

Griffin, et al., "Specific Covalent Labeling of Recombinant Protein Molecules Inside Live Cells", Science, 1998, vol. 281, pp. 269-272.

Karramkam, et al., "2-,3- and 4-[18F]Fluoropyridine by no-carrier-added nucleophilic aromatic substitution with K [18F]F-K222—a comparative study", J. Label Compd. Radiopharm, 2003, vol. 46, pp. 979-992.

Långström, et al., "Compounds Labelled with Short-Lived β+ -Emitting Radionuclides and Some Applications in Life Sciences. The Importance of Time as a Parameter", Acta Chemica Scandinavica, 1999, vol. 53, pp. 651-669.

Machleidt, et al., "Protein Labeling With FlAsH and ReAsH", Methods in Molecular Biology, vol. 356, pp. 209-220.

Martin, et al., "Mammalian cell-based optimization of the biarsenical-binding tetracysteine motif for improved fluorescence and affinity", Nature Biotechnology, 2005, vol. 23, No. 10, pp. 1308-1314.

McCarthy, "Recent Advances in the Design and Synthesis of Carbon-14 Labelled Pharmaceuticals from Small Molecule Precursors", Current Pharmaceutical Design, 2000, vol. 6, pp. 1057-1083.

Saljoughian, "Synthetic Tritium Labeling: Reagents and Methodologies", Synthesis, 2002, No. 13, pp. 1781-1801.

Wilkins, et al., "Photochemical control of FlAsH labeling of proteins", Bioorganic & Medicinal Chemistry Letters, 2009, vol. 19, pp. 4296-4298.

Yang, et al., "A Convenient Preparation of Xanthene Dyes", J. Org. Chem., 2005, vol. 70, pp. 6907-6912.

International Search Report of corresponding PCT Application No. PCT/EP2011/070172 mailed May 8, 2012.

\* cited by examiner

AGENTS AND METHODS FOR VISUALIZING ANALYTES

This application is the U.S. national stage of PCT/EP2011/070172, filed Nov. 15, 2011 and published in English as WO 2012/066006 A1 on May 12, 2012, which claims the benefit of priority under 35 U.S.C. §119 to United Kingdom application serial no. 1019303.5, filed Nov. 15, 2010, all of which applications and publication are incorporated herein by reference.

BACKGROUND

The current invention relates to radioactively labeled compounds that find use in the visualization and analysis of compounds, particularly compounds containing or attached to a tetracysteine moiety.

Biarsenical compounds are known from, for example, Griffin et. al. *Science* 1998, 281, 269-272, Adams et. al. *J. Am. Chem. Soc.* 2002, 124, 6063-6076, Genin et. al. *J. Am. Chem. Soc.* 2008, 130, 8596-8597, Wilkins et. al. *Bioorg. Med. Chem. Lett.* 2009, 19, 4296-4298, Machleidt et. al. *Meth. Mol. Biol.* 2006, 356, 209-220, WO2007144077, WO2005040197, US20030083373, and WO03107010. These biarsenical compounds expose suitably located arsenic moieties. The specifically-located arsenic moieties bind strongly to tetracysteine sequences. Tetracysteine sequences are inherent features of some proteins. In other proteins, they may be inserted into the sequence, for example as a tag. A tetracysteine sequence may alternatively be present in a tag that associates non-covalently with a peptide or other compound.

The development of such biarsenical compounds was driven by an interest in the fields of molecular biology and medicine to enable visualisation of biologically relevant molecules by fluorescence tagging; for example for determining the location of a protein, or other biomolecule, within, for example, a cell or tissue.

Because the advent of biarsenical compounds was exclusively dependent on fluorescence for detection, biarsenicals are typically based on well established fluorescent compounds or cores, such as xanthene dyes including fluorones and fluoresceins. Such dyes have long been utilised in a variety of mapping and probing studies, all depending on the fluorescent properties of the dye, and may be prepared by methods such as those recently described in Jorge et. al. *J. Org. Chem.* 2005, 70, 6907-6912.

While biarsenical probes have been useful, their applicability is limited by the dependence on fluorescence detection. For example, organic dyes are well known to suffer from classical photobleaching, which constitutes an inherent drawback. Other aspects which hamper the extension of biarsenical probing include a relatively high detection limit (micromolar range) as well as poor penetration of the fluorescence signal (blue to red wavelength light), which precludes applications in complex matrices, such as in vivo. Despite these drawbacks, biarsenical compounds have been widely used and their binding to various protein structures has been widely studied.

US2003/0083373 is directed to the provision of biarsenical molecules, in particular fluorescein derivatives containing carboxyl groups. That document makes reference to carboxyfluoroscein derivatives containing $^3$H or $^{125}$I. However, no synthesis details or data concerning radiolytic stability is provided for those compounds. US2003/0083373 exclusively provides synthesis details for biarsenicals by preparation from commercially available 2-arboxyphenylfluorones/fluoresceins.

The carboxylic acid group in such fluorescein analogues constitutes a site of high reactivity, and can interact with radiolabelling reagents. Any synthetic approach to such molecules would be complicated, likely requiring the use of protecting groups, having a negative impact on synthesis timeframe which is very critical in shortlived radiochemical synthesis. In fact, it is likely that the compounds mentioned in US2003/0083373 cannot be prepared using available radiochemical methodology.

A further drawback of such carboxy-fluorescein compounds is that they are subject to tautomerism, which greatly complicates synthesis, purification, and distribution in the study matrix of interest.

DESCRIPTION OF THE INVENTION

In a first aspect, this invention provides a compound of formula I:

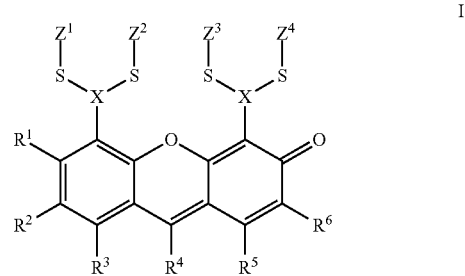

wherein
X is As or P,
$Z^1$-$Z^4$ are each independently lower alkyl, or $Z^1$ and $Z^2$ or $Z^3$ and $Z^4$, or both, together form an ethylene or propylene chain, which may optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —CONH$_2$, —CONH($C_1$-$C_6$ alkyl), —CON($C_1$-$C_6$ alkyl)$_2$, and —NHCO($C_1$—$C_6$ alkyl);

$R^1$ and $R^4$ are each independently selected from the group consisting of hydrogen, halogen, hydroxy, formyl, cyano, —CONH$_2$, —CONH($C_1$-$C_6$ alkyl), —CON($C_1$-$C_6$ alkyl)$_2$, —NHCO($C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkyl amino, mono or di- $C_6$-$C_{10}$ arylamino, $C_1$-$C_6$ alkylthio, $C_6$-$C_{10}$ arylthio, halogen, hydroxy, formyl, cyano, —CONH$_2$, —CONH(C$_1$-C$_6$ alkyl), —CON(C$_1$-C$_6$ alkyl)$_2$, and —NHCO(C$_1$-C$_6$ alkyl);

R$^2$, R$^3$, R$^5$ and R$^6$ are each independently selected from the group consisting of hydrogen, halogen, formyl, cyano, —CONH$_2$, —CONH(C$_1$-C$_6$ alkyl), —CON(C$_1$-C$_6$ alkyl)$_2$, —NHCO(C$_1$-C$_6$ alkyl), C$_1$-C$_6$ alkyl optionally substituted by one or more halogens, C$_2$-C$_6$ alkenyl, C$_2$-C$_4$ alkynyl, C$_6$-C$_{10}$ aryl, C$_6$-C$_{10}$ heteroaryl, C$_1$-C$_6$ acyl, C$_6$-C$_{10}$ aroyl, C$_1$-C$_6$ alkoxy, C$_6$-C$_{10}$ aryloxy, di- C$_1$-C$_6$ alkylamino, di- C$_6$-C$_{10}$ arylamino, C$_1$-C$_6$ alkylthio and C$_6$-C$_{10}$ arylthio, wherein said C$_1$-C$_6$ alkyl, C$_6$-C$_{10}$ aryl, C$_6$-C$_{10}$ heteroaryl, C$_1$-C$_6$ acyl, C$_6$-C$_{10}$ aroyl, C$_1$-C$_6$ alkoxy, C$_6$-C$_{10}$ aryloxy, di- C$_1$-C$_6$ alkylamino, di- C$_6$-C$_{10}$ arylamino, C$_1$-C$_6$ alkylthio and C$_6$-C$_{10}$ arylthio may each optionally be substituted by one or more substituents independently selected from the group consisting of C$_1$-C$_6$ alkyl optionally substituted by one or more halogens, C$_2$-C$_6$ alkenyl, C$_2$-C$_4$ alkynyl, C$_6$-C$_{10}$ aryl, C$_1$-C$_6$ acyl, C$_6$-C$_{10}$ aroyl, C$_1$-C$_6$ alkoxy, C$_6$-C$_{10}$ aryloxy, di- C$_1$-C$_6$ alkyl amino, di- C$_6$-C$_{10}$ arylamino, C$_1$-C$_6$ alkylthio, C$_6$-C$_{10}$ arylthio, halogen, formyl, cyano, —CONH$_2$, —CONH(C$_1$-C$_6$ alkyl), —CON(C$_1$-C$_6$ alkyl)$_2$, and —NHCO(C$_1$-C$_6$ alkyl); and at least one of R$^1$-R$^6$ comprises an isotope atom.

The compound of formula I is useful as an isotopically-labeled (for example radiolabeled) biarsenical probe, for example, in methods for visualising a tetracysteine-tagged analyte molecule. The isotopically labeled compounds of the invention can be readily prepared, and obtained in sufficient quantity to be useful as probes for the visualization of molecules.

In a second aspect, this invention provides a method for visualising a tetracysteine-tagged analyte molecule comprising contacting said tetracysteine-tagged analyte molecule with a compound of formula I, as defined above.

In a third aspect, the present invention provides a kit comprising a precursor molecule, and optionally one or more of instructions for converting the precursor into a compound of formula I, and optionally a reagent that provides the isotope (for example radioactive) group, other reagents, handling instructions, safety information, or scientific background material. The invention also provides a kit comprising a first compound of formula I, and a second compound of formula I, wherein said first and second compounds of formula I differ only in that they comprise a different isotope atom. The invention also provides a kit comprising a first complex formed between a first compound of formula I and a first sample of a tetra-cysteine tagged molecule; and
a second complex formed between a second compound of formula I and a second sample of the tetra-cysteine tagged molecule, wherein said first and second compounds of formula I differ only in that they comprise a different isotope atom.

In a fourth aspect, the present invention provides methods for synthesising a compound of formula I. The invention also provides intermediates of formula II, IIA, III and IIIA.

In a fifth aspect, this invention provides nonlabeled novel compounds of formula I, useful as reference substances within radiochemical research and development relevant to biarsenical probes. In particular, compounds of general formula I, wherein R$^2$ is methoxy and/or R$^4$ is 4-fluorophenyl are useful.

In a sixth aspect, the present invention provides a complex between a tetracysteine-tagged analyte molecule, as defined above, and a compound of formula I, as defined above. Such complex is characterised by a high binding affinity, through the multiple As/PS interactions, and may be isolated and characterised by methods known in the art, for example NMR, radiodetection or mass spectroscopy.

In a seventh aspect, the present invention provides a method for the treatment or prophylaxis of cancer or other hyperproliferative disorders in a mammal, which comprises administering to the mammal a therapeutically effective amount of a compound of formula I as defined above, wherein at least one of R$^1$-R$^6$ comprises a radioactive isotope atom, optionally in the form of a complex with a tetracysteine-tagged biomolecule, such as a peptide, a protein or an antibody.

DETAILED DESCRIPTION OF THE INVENTION

Figure 1A:
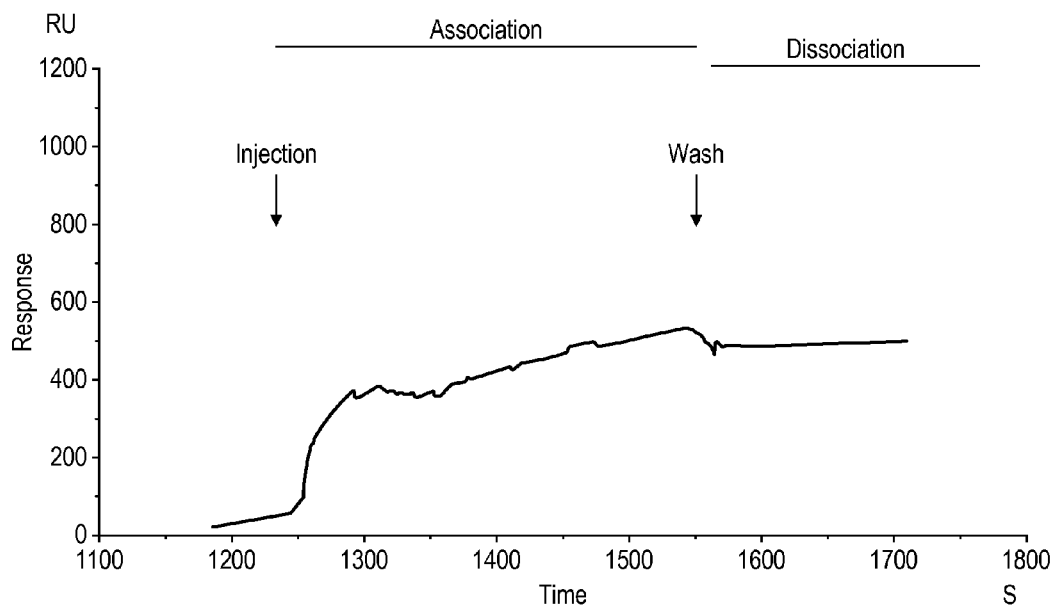
FIG. 1(A) shows the real time interaction of PSMXB-6 with immobilised Biotin-His-Arg-Trp-Cys-Cys-Pro-Gly-Cys-Cys-Lys-Thr, [SEQ ID NO 1] using surface plasmon resonance technology (BiaCore 3000). 100 µM PSMXB-6 was injected over a sensor chip with immobilized Biotin-His-Arg-Trp-Cys-Cys-Pro-Gly-Cys-Cys-Lys-Thr-Phe [SEQ ID NO 2].

The present invention enables the provision of one or more isotopically labeled (such as radiolabeled) biarsenical probes according to formula I, which are of the same constitution regardless of which isotope, for example radioactive atom, or atoms is used, but which can have the most appropriate radioactive atom present for the intended application. As such, the invention provides for the unique opportunity of visualising the same tetracysteine tagged analyte of interest in a variety of matrices and settings, by selecting a suitable radioisotope and yet maintaining the chemical constitution, and hence properties, of the probe (i. e. compound of formula I).

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups.

As used herein, the term "alkoxy" means the group O-alkyl, where "alkyl" is used as described above. Examples of alkoxy groups include methoxy and ethoxy groups. Other examples include propoxy and butoxy.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl.

As used herein, the term "aryl" means a monocyclic or bicyclic aromatic carbocyclic group. Examples of aryl groups include phenyl and naphthyl. In a bicyclic aromatic group, one of the rings may, for example, be partially saturated. Examples of such groups include indanyl and tetrahydronaphthyl.

As used herein, the term "heteroaryl" means an aromatic cyclic group of carbon atoms wherein from one to three of the carbon atoms is/are replaced by one or more heteroatoms independently selected from nitrogen, oxygen or sulfur. A heteroaryl group may, for example, be monocyclic or bicyclic. In a bicyclic heterocyclyl group there may be one or more heteroatoms in each ring, or only in one of the rings. A heteroatom is preferably O or N.

As used herein, the term "halogen" means fluorine, chlorine, bromine or iodine.

A compound of formula I, especially in labelled, such as radiolabelled form, is sometimes referred to as a probe.

As used herein, "protein" is intended to include any molecule which contains peptide bonds.

The compounds of the invention comprise at least one isotope atom (i.e. at least one of $R^1$-$R^6$ comprises an isotope atom). Herein, an "isotope atom" is an atom of an element that is not the most common naturally occurring isotope. The isotope atom is present in bulk material of a compound of the invention at a level higher than its naturally occurring proportion. Preferably, the compounds of the invention contain from 1 to 2 isotope atoms. In one preferred embodiment, the compounds of the invention contain 1 isotope atom. In another embodiment, the compounds of the invention contain 2 isotope atoms, in which case the isotope atoms may be the same or, more preferably, different.

Isotope atoms may be radioactive, or they may not be radioactive. Detectable radioactive atoms (isotopes), useful in the context of the present invention include, for use in PET: $^{11}$C, $^{18}$F, $^{75}$Br, $^{76}$Br and $^{120}$I, for use in SPECT: $^{123}$I and $^{131}$I, and, for detection in in-vitro, tissue, and post-mortem samples: $^{3}$H, $^{14}$C and $^{125}$I. The most preferred radioactive atoms are $^{11}$C, $^{18}$F, $^{123}$I, $^{19}$F, $^{3}$H and $^{14}$C. For MRI-applications, the non-radioactive isotopes $^{19}$F and $^{13}$C are useful. Preferably, an isotope atom is a radioactive atom. (i.e. at least one of $R^1$-$R^6$ comprises a radioactive isotope atom).

Preferably, X is As.

In the context of the present invention, unless stated otherwise, the term optionally substituted indicates the optional presence of one or more substituents independently selected from the list consisting of $C_1$-$C_6$ alkyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkyl amino, mono- or di- $C_6$-$C_{10}$ arylamino, $C_1$-$C_6$ alkylthio, $C_6$-$C_{10}$ arylthio, halogen, hydroxy, formyl, cyano, —$CONH_2$, —$CONH(C_1$-$C_6$ alkyl), —$CON(C_1$-$C_6$ alkyl)$_2$, and —$NHCO(C_1$-$C_6$ alkyl). Preferred optional substituents include $C_1$-$C_6$ alkyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano,
—$CONH_2$, —$CONH(C_1$-$C_6$ alkyl), —$CON(C_1$-$C_6$ alkyl)$_2$, and —$NHCO(C_1$-$C_6$ alkyl). In some embodiments, the optional substituents may each independently be selected from the group consisting of $C_1$-$C_3$ alkyl, $C_6$ aryl, $C_1$-$C_3$ acyl, $C_6$ aroyl, $C_1$-$C_3$ alkoxy, $C_6$ aryloxy, di- $C_1$-$C_3$ alkyl amino, di- $C_6$ arylamino, $C_1$-$C_3$ alkylthio, $C_6$ arylthio, halogen, hydroxy, formyl, cyano, —$CONH_2$, —$CONH(C_1$-$C_3$ alkyl), —$CON(C_1$-$C_3$ alkyl)$_2$, and —$NHCO(C_1$-$C_3$ alkyl). In other embodiments, the optional substituents may each independently be selected from the group consisting of halogen, $C_1$-$C_6$ alkyl, $C_1$-$C_6$ alkoxy, di- $C_1$-$C_6$ alkylamino, and cyano.

It is preferred that each optionally substituted group carries a single optional substituent as defined above, though more than one optional substituent may be present where valency and steric factors permit. For example, 2 or 3 substituents may be present on an optionally substituted group.

Preferably, $Z^1$-$Z^4$ are independently lower alkyl, or $Z^1$ and $Z^2$ or $Z^3$ and $Z^4$, or both, together form an ethylene or propylene chain, which alkyl, ethylene or propylene chain may optionally be substituted by one or more substituents independently selected from the group consisting of halogen and $C_1$-$C_3$ alkoxy. More preferably, $Z^1$-$Z^4$ are independently $C_{1-6}$ alkyl, or $Z^1$ and $Z^2$ or $Z^3$ and $Z^4$, or both, together form an ethylene or propylene chain (i.e. the compound of formula I preferably does not comprise any optional substituents in the groups $Z^1$-$Z^4$). Preferably, $Z^1$ and $Z^2$ together represent alkylene, such as ethylene, and $Z^3$ and $Z^4$ together represent alkylene, such as ethylene.

Preferably at least one of $R^1$, $R^3$, $R^4$, and $R^5$ comprises an isotope (e.g. radioactive) atom. Compounds which contain an isotope atom at $R^1$, $R^3$, $R^4$ and/or $R^5$ have particularly good radiolytic stability, since those isotope atoms are not located at positions ortho to carbonyl groups. Compounds containing isotope atoms ortho to carbonyl groups may have decreased stability due to tautomeric effects associated with carbonyl groups. Thus, in one embodiment, the compounds of the invention do not contain an isotope atom at $R^2$ or $R^6$.

More preferably, at least one of $R^1$ and $R^4$ comprises an isotope (e.g. radioactive) atom. In one embodiment $R^1$ comprises an isotope (e.g. radioactive) atom. In another embodiment, $R^4$ comprises an isotope (e.g. radioactive) atom. In another embodiment, $R^1$ and $R^4$ each comprise an isotope (e.g. radioactive) atom. Preferred such radioactive atoms are $^3$H, $^{11}$C, $^{14}$C, and $^{18}$F.

When $R^1$ comprises a radioactive atom, preferably $R^1$ is $C_1$-$C_6$ alkoxy, for example methoxy, i.e. $H_3^{14}CO$—, $H_3^{11}CO$— or $^3H_nH_{3-n}CO$—, where n is 1, 2, or 3, whereof n=3 is preferred.

When $R^4$ comprises a radioactive atom, preferably $R^4$ is fluoroaryl, such as fluorophenyl, especially 4-fluorophenyl. Such $R^4$ group may comprise $^{18}$F, which is preferred, or $^{11}$C, $^{14}$C, or $^3$H.

Alternatively, when $R^4$ comprises a radioactive atom, preferably $R^4$ is iodoaryl, such as iodophenyl, especially 4-iodophenyl. Such $R^4$ group may comprise $^{120}$I, $^{123}$I, $^{125}$I or $^{131}$I.

In another preferred embodiment, $R^4$ is $C_6$-$C_{10}$ aryl (e.g. phenyl) substituted by $C_1$-$C_3$ alkoxy. In that preferred embodiment, the $C_1$-$C_3$ alkoxy is, for example, methoxy, i.e. $H_3^{14}CO$—, $H_3^{11}CO$— or $^3H_nH_{3-n}CO$—, where n is 1, 2, or 3, whereof n=3 is preferred.

In another preferred embodiment, $R^4$ is $C_6$-$C_{10}$ aryl (e.g. phenyl) substituted by mono- or di- $C_1$-$C_6$ alkyl amino. In that preferred embodiment, the mono- or di- $C_1$-$C_6$ alkyl amino is, for example, methylamino or dimethylamino, i.e. $NH^{11}CH_3$, $NH^{14}CH_3$, or $NHC^3H_nH_{3-n}$ where n is 1, 2, or 3, whereof n=3 is preferred; or $NCH_3(^{11}CH_3)$, $NCH_3(^{14}CH_3)$, or $NCH_3(C^3H_nH_{3-n})$ where n is 1, 2 or 3, whereof n=3 is preferred.

Preferably, $R^1$ is selected from the group consisting of hydroxy, $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-6}$ alkoxy, mono or di- $C_1$-$C_6$ alkyl amino, and cyano. More preferably, $R^1$ is selected from the group consisting of hydroxy, $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-6}$ alkoxy, di- $C_1$-$C_6$ alkyl amino, and cyano. Still more preferably, $R^1$ is hydroxy or $C_1$-$C_6$ alkoxy. Yet more preferably, $R^1$ is $C_1$-$C_6$ alkoxy. In one preferred embodiment, $R^1$ is methoxy. In another embodiment, $R^1$ is hydroxy or methoxy.

Preferably, $R^4$ is halogen, formyl, —$CONH_2$, —CONH($C_1$-$C_6$ alkyl), —CON($C_1$-$C_6$ alkyl)$_2$, —NHCO($C_1$-$C_6$ alkyl), $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio, wherein said $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkyl amino, mono or di- $C_6$-$C_{10}$ arylamino, $C_1$-$C_6$ alkylthio, $C_6$-$C_{10}$ arylthio, halogen, hydroxy, formyl, cyano, —$CONH_2$, —CONH($C_1$-$C_6$ alkyl), —CON($C_1$-$C_6$ alkyl)$_2$, and —NHCO($C_1$-$C_6$ alkyl). More preferably, $R^4$ is halogen, $C_6$-$C_{10}$ aryl or $C_6$-$C_{10}$ heteroaryl, wherein said $C_6$-$C_{10}$ aryl or $C_6$-$C_{10}$ heteroaryl may each optionally be substituted by one or more substituents independently selected from the group consisting of $C_1$-$C_6$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano. In one preferred embodiment, $R^4$ is halogen, $C_6$-$C_{10}$ aryl or $C_6$-$C_{10}$ heteroaryl, wherein said $C_6$-$C_{10}$ aryl or $C_6$-$C_{10}$ heteroaryl may each optionally be substituted by one or more substituents independently selected from the group consisting of $C_1$-$C_6$ alkyl optionally substituted by one or more halogens, $C_{2-4}$ alkenyl, $C_{2-4}$ alkynyl, $C_{1-3}$ alkoxy, di- $C_1$-$C_6$ alkyl amino, and cyano. Still more preferably, $R^4$ is $C_6$-$C_{10}$ aryl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano. Yet more preferably, $R^4$ is $C_6$-$C_{10}$ aryl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, di- $C_1$-$C_6$ alkyl amino, and cyano.

In one preferred embodiment, $R^4$ is phenyl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano. In another preferred embodiment, $R^4$ is phenyl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, di- $C_1$-$C_6$ alkyl amino, and cyano. In another preferred embodiment, $R^4$ is phenyl optionally substituted with up to three halogens. In another preferred embodiment, $R^4$ is 4-fluorophenyl.

In one preferred embodiment, $R^4$ is optionally substituted phenyl containing at least one $^{11}C$, or $^{14}C$, wherein said phenyl may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano. In one preferred embodiment, $R^4$ is phenyl substituted with one or more of $NHC^3H_3$, $NH^{11}CH_3$, $NH^{14}CH_3$, $NCH_3(C^3H_3)$, $NCH_3(^{11}CH_3)$, $NCH_3(^{14}CH_3)$, $^{76}Br$, $^{123}I$, $^{125}I$, $^{131}I$, $^3H$, or $^{18}F$.

Preferably, $R^2$, $R^3$, $R^5$ and $R^6$ are each independently selected from the group consisting of hydrogen, halogen, $C_1$-$C_3$ alkyl and $C_1$-$C_3$ alkoxy. In a further preferred embodiment, at least two, such as three, and preferably all, of $R^2$, $R^3$, $R^5$, and $R^6$ are hydrogen.

In one preferred embodiment, $R^2$ and $R^6$ are hydrogen; and at least one of $R^1$, $R^3$, $R^4$, and $R^5$ comprises an isotope atom.

In another preferred embodiment, $R^2$, $R^3$, $R^5$ and $R^6$ are hydrogen; and at least one of $R^1$ and $R^4$ comprises an isotope atom.

In a preferred embodiment, the compound of formula I, as defined above, does not comprise any optional substituents in the groups $Z^1$-$Z^4$ and $R^1$-$R^6$.

In another preferred embodiment, $R^1$ is selected from the group consisting of hydroxy, $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-6}$ alkoxy, mono or di- $C_1$-$C_6$ alkyl amino, and cyano; and at least one of $R^1$ and $R^4$ comprises an isotope atom.

In another preferred embodiment, $R^4$ is $C_6$-$C_{10}$ aryl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano; and at least one of $R^1$ and $R^4$ comprises an isotope atom.

In another preferred embodiment, X is As; $Z^1$-$Z^4$ are independently $C_{1-6}$ alkyl, or $Z^1$ and $Z^2$ or $Z^3$ and $Z^4$, or both, together form an ethylene or propylene chain;
$R^4$ is halogen, formyl, —$CONH_2$, —CONH($C_1$-$C_6$ alkyl), —CON($C_1$-$C_6$ alkyl)$_2$, —NHCO($C_1$-$C_6$ alkyl), $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio, wherein said $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkyl amino, mono or di- $C_6$-$C_{10}$ arylamino, $C_1$-$C_6$ alkylthio, $C_6$-$C_{10}$ arylthio, halogen, hydroxy, formyl, cyano, —$CONH_2$, —CONH($C_1$-$C_6$ alkyl), —CON($C_1$-$C_6$ alkyl)$_2$, and —NHCO($C_1$-$C_6$ alkyl); and at least one of $R^1$ and $R^4$ comprises an isotope atom.

In another preferred embodiment, X is As; $Z^1$-$Z^4$ are independently $C_{1-6}$ alkyl, or $Z^1$ and $Z^2$ or $Z^3$ and $Z^4$, or both, together form an ethylene or propylene chain; $R^2$, $R^3$, $R^5$ and $R^6$ are each hydrogen; $R^1$ is selected from the group consisting of hydroxy, $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano; $R^4$ is $C_6$-$C_{10}$ aryl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano; and at least one of $R^1$ and $R^4$ comprises an isotope atom.

In another preferred embodiment, X is As; $Z^1$-$Z^4$ are independently $C_{1-6}$ alkyl, or $Z^1$ and $Z^2$ or $Z^3$ and $Z^4$, or both, together form an ethylene or propylene chain; $R^2$, $R^3$, $R^5$ and $R^6$ are each hydrogen; $R^1$ is selected from the group consisting of $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, di- $C_1$-$C_6$ alkyl amino, and cyano; $R^4$ is $C_6$-$C_{10}$ aryl optionally substituted with up to three substituents independently selected from halogen, $C_{1-6}$alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano; and at least one of $R^1$ and $R^4$ comprises an isotope atom.

In another preferred embodiment, X is As; $Z^1$-$Z^4$ are independently $C_{1-6}$ alkyl, or $Z^1$ and $Z^2$ or $Z^3$ and $Z^4$, or both, together form an ethylene or propylene chain; $R^2$, $R^3$, $R^5$ and $R^6$ are each hydrogen; $R^1$ is selected from the group consisting of hydroxy, $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano; $R^4$ is $C_6$-$C_{10}$ aryl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, di- $C_1$-$C_6$ alkyl amino, and cyano; and at least one of $R^1$ and $R^4$ comprises an isotope atom.

In another preferred embodiment, X is As; $Z^1$-$Z^4$ are independently $C_{1-6}$ alkyl, or $Z^1$ and $Z^2$ or $Z^3$ and $Z^4$, or both, together form an ethylene or propylene chain; $R^2$, $R^3$, $R^5$ and $R^6$ are each hydrogen; $R^1$ is $C_1$-$C_6$ alkoxy; $R^4$ is $C_6$-$C_{10}$ aryl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, di- $C_1$-$C_6$ alkyl amino, and cyano; and at least one of $R^1$ and $R^4$ comprises an isotope atom.

In another preferred embodiment,
a) $R^1$ is hydroxy or methoxy; and
either $R^4$ is optionally substituted phenyl containing at least one $^{11}C$, or $^{14}C$, wherein said phenyl may optionally be substituted with up to three substituents independently selected from halogen, $C_{1-6}$alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano,
or $R^4$ is phenyl substituted with one or more of $NHC^3H_3$, $NH^{11}CH_3$, $NH^{14}CH_3$, $NCH_3(C^3H_3)$, $NCH_3(_{11}CH_3)$, $NCH_3(^{14}CH_3)$, $^{76}Br$, $^{123}I$, $^{125}I$, $^{131}I$, $^3H$, or $^{18}F$;
or:
b) $R^1$ is selected from the group consisting of $C^3H_3O$, $^{11}CH_3O$, and $^{14}CH_3O$; and
$R^4$ is phenyl optionally substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono or di- $C_1$-$C_6$ alkyl amino, and cyano.

In another preferred embodiment,
$Z^1$ and $Z^2$, and $Z^3$ and $Z^4$, respectively, together represent ethylene;
$R^2$, $R^3$, $R^5$, and $R^6$ are hydrogen;
a) $R^1$ is methoxy; and
either $R^4$ is optionally substituted phenyl containing at least one $^{11}C$, or $^{14}C$, wherein said phenyl may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-3}$alkoxy, mono or di- $C_1$-$C_6$ alkyl amino, and cyano
or $R^4$ is phenyl substituted with one or more of $NHC^3H_3$, $NH^{11}CH_3$, $NH^{14}CH_3$, $NCH_3(C^3H_3)$, $NCH_3(_{11}CH_3)$, $NCH_3(^{14}CH_3)$, $^{76}Br$, $^{123}I$, $^{125}I$, $^{131}I$, $^3H$, or $^{18}F$;
or:
b) $R^1$ is selected from the group consisting of $C^3H_3O$, $^{11}CH_3O$, and $^{14}CH_3O$; and
$R^4$ is 4-fluorophenyl.

In a preferred embodiment, the compound of formula I, as defined above, does not comprise any optional substituents in the groups $Z^1$-$Z^4$ and $R^1$-$R^6$.

In an especially preferred embodiment, all of $R^2$, $R^3$, $R^5$, and $R^6$ are hydrogen, $R^1$ is $C_1$-$C_6$ alkoxy, for example methoxy, $R^4$ is fluoroaryl, for example fluorophenyl, especially 4-fluorophenyl, $Z^1$ and $Z^2$ together represent ethylene, $Z^3$ and $Z^4$ together represent ethylene, and either $R^1$ or $R^4$ comprises one, which is preferred, or more radioactive atoms. In this embodiment, $R^4$ typically contains $^{18}F$, whereas $R^1$ typically contains one of $^{11}C$, u or one or more of $^3H$.

The invention also provides compounds of formula I wherein X is As; $Z^1$-$Z^4$ are independently lower alkyl, or $Z^1$ and $Z^2$ or $Z^3$ and $Z^4$, or both, together form an ethylene or propylene chain, which may optionally be substituted; $R^1$-$R^6$ are independently selected from the group consisting of hydrogen, optionally substituted $C_1$-$C_6$ alkyl, optionally substituted $C_6$-$C_{10}$aryl, optionally substituted $C_1$-$C_6$ acyl, optionally substituted $C_6$-$C_{10}$ aroyl, optionally substituted $C_1$-$C_6$ alkoxy, optionally substituted $C_6$-$C_{10}$ aryloxy, optionally substituted mono or di- $C_1$-$C_6$ alkyl amino, optionally substituted mono or di- $C_6$-$C_{10}$ arylamino, optionally substituted $C_1$-$C_6$ alkylthio, optionally substituted $C_6$-$C_{10}$ arylthio, halogen, hydroxy, formyl, carboxyl, amino, cyano, —$CONH_2$, —$CONH(C_1$-$C_6$ alkyl), —$CON(C_1$-$C_6$ alkyl)$_2$, —$NHCO(C_1$-$C_6$ alkyl), and at least one of $R^1$-$R^6$ comprises an isotope atom. In that embodiment, preferably $R^1$-$R^6$ are independently selected from the group consisting of optionally substituted $C_1$-$C_6$ acyl, optionally substituted $C_6$-$C_{10}$ aroyl, optionally substituted $C_1$-$C_6$ alkoxy, optionally substituted $C_6$-$C_{10}$ aryloxy, optionally substituted mono- or di- $C_1$-$C_6$ alkyl amino, optionally substituted mono- or di- $C_6$-$C_{10}$ arylamino, optionally substituted $C_1$-$C_6$ alkylthio, optionally substituted $C_6$-$C_{10}$ arylthio, halogen, formyl, carboxyl, amino, cyano, —$CONH_2$, —$CONH(C_1$-$C_6$ alkyl), —$CON(C_1$-$C_6$ alkyl)$_2$, —$NHCO(C_1$-$C_6$ alkyl). More preferably, $R^1$-$R^6$ are independently selected from the group consisting of optionally substituted $C_1$-$C_6$ acyl, optionally substituted $C_6$-$C_{10}$ aroyl, optionally substituted $C_1$-$C_6$ alkoxy, optionally substituted $C_6$-$C_{10}$ aryloxy, optionally substituted mono- or di- $C_1$-$C_6$ alkyl amino, optionally substituted mono- or di- $C_6$-$C_{10}$ arylamino, optionally substituted $C_1$-$C_6$ alkylthio, optionally substituted $C_6$-$C_{10}$ arylthio, halogen, formyl, cyano, —$CONH_2$, —$CONH(C_1$-$C_6$ alkyl), —$CON(C_1$-$C_6$ alkyl)$_2$, —$NHCO(C_1$-$C_6$ alkyl). Preferably, $R^4$ is optionally substituted optionally substituted $C_6$-$C_{10}$aryl, and at least one of $R^1$ and $R^4$ contains at least one radioactive atom. More preferably,
a) $R^1$ is hydroxy or methoxy; and $R^4$ is optionally substituted phenyl containing at least one $^{11}C$, or $^{14}C$, or phenyl substituted with one or more of $NHC^3H_3$, $NH^{11}CH_3$, $NH^{14}CH_3$, $NCH_3(C^3H_3)$, $NCH_3(^{11}CH_3)$, $NCH_3(^{14}CH_3)$, $^{76}Br$, $^{123}I$, $^{125}I$, $^{131}I$, $^3H$, or $^{18}F$; or
b) $R^1$ is selected from the group consisting of $C^3H_3O$, $^{11}CH_3O$, and $^{14}CH_3O$, and $R^4$ is optionally substituted phenyl; and at least one of $R^1$-$R^6$ comprises an isotope (e.g. a radioactive isotope) atom. Still more preferably, $Z^1$ and $Z^2$, and $Z^3$ and $Z^4$, respectively, together represent ethylene; $R^2$, $R^3$, $R^5$, and $R^6$ are hydrogen, and a) $R^1$ is methoxy, and $R^4$ is optionally substituted phenyl containing at least one of $^{11}C$ or $^{14}C$, or phenyl substituted with one of $NHC^3H_3$, $NH^{11}CH_3$, $NH^{14}CH_3$, $NCH_3(C^3H_3)$, $NCH_3(^{11}CH_3)$, $NCH_3(^{14}CH_3)$, $^{76}Br$, $^{123}I$, $^{125}I$, $^{131}I$, $^3H$, or $^{18}F$; or b) $R^1$ is selected from the group consisting of $C^3H_3O$, $^{11}CH_3O$, and $^{14}CH_3O$, and $R^4$ is 4-fluorophenyl.

A preferred embodiment of the present invention is one which allows for utilising, in different distinct molecules, several relevant isotopes (for example radioactive isotopes) within a probe compound according to formula I. Such embodiment provides for replacing one or more of relevant atoms with isotopes, such as radioactive isotopes, without changing the constitution of the probe of formula I. Therefore preferred embodiments of the present invention are those which combine at least two of, preferably three of, or all four of fluorine, iodine, hydrogen, and carbon at positions which allow for practical radiosynthesis of the respective isotopically labelled compounds. For example, a compound of formula I which incorporates an iodine or a fluorine isotope atom, of which fluorine is generally preferred, as well as a functionality which may comprise hydrogen or carbon isotope atoms (for example radioactive isotopes) is preferred. Typically, the latter is $R^1$, selected from $C_1$-$C_6$ alkoxy, such as methoxy, i. e. $^3H_nH_{3-n}C-$, where n is 1, 2, or 3, whereof the latter is preferred, or $H_3{}^{14}C-$, or $H_3{}^{11}C-$.

Preferred compounds of formula I which comprise one or more stable isotopes, typically $^2H$, $^{19}F$ or $^{13}C$, are of the same constitution as those preferred embodiments of radiolabeled compounds of formula I presented above. In addition, for the compounds of formula I containing $^{19}F$, a particularly preferred group of compounds comprise the $C^{19}F_3O-$ group at the $R^1$ position.

Preferred compounds of the invention comprise 2 or more atoms or groups which may be isotope (e.g. radioactive isotope) atoms. Those compounds permit visualization and analysis using different techniques with the same compound of the invention, and enabling translation of results between matrices, e. g. in vitro autoradiography, in vivo PET, in vivo SPECT or in vivo MRI, using multiple differently labeled probes of the same chemical constitution (other than the presence of different isotope atoms).

This invention also provides a method for visualising a tetracysteine-tagged analyte molecule comprising contacting said tetracysteine-tagged analyte molecule with a compound of formula I.

In the method, a compound of formula I is introduced into the sample by the known routes and methods, and radiation is detected by means of standard equipment and methodology. For example, phosphor imaging, positron emission tomography, photographic film imaging, single photon emission computed tomography, scintillation detection, mass spectrometry or accelerated mass spectrometry may be used to detect the radiation from the sample. A non-radioactive label may be detected by other suitable means, for example NMR, MRI or mass spectrometry or accelerated mass spectrometry.

The method provides for analysing the location (i.e. mapping or probing), visualising, locating, measuring, or quantifying of any analyte molecule of interest, provided that the analyte molecule carries appropriately situated cysteine residues. An advantage of the present method, is that knowledge, additives, workup procedures, modes of application or sample preparation in the prior art related to fluorescent mapping using biarsenical compounds may be directly and uneventfully used in the method.

In one embodiment, the analyte molecule is provided into the matrix of interest prior to the subsequent introduction of the probe (pretargeting).

In another embodiment, the complex made up of the analyte molecule bound to the probe is provided into the matrix of interest.

Another advantage of the methods provided herein is that the same probe (i. e. of identical constitution) may be applied in a whole range of studies, involving e. g. studies performed in vitro, such as on cells, organelles, tissues, or any other relevant matrix, and studies performed in vivo, such as in microbes, whole animals, or humans. The person skilled in the art is capable of selecting an appropriate radioactive atom or group, associated with a suitable form of radiation, for each potential application. The present invention provides the unique opportunity to select and incorporate various radioactive atoms or groups, or other relevant isotopes, including, but not limited to, e.g. $^3H$, $^{11}C$, $^{14}C$, $^{18}F$, into a single, structurally distinct probe. One simple example, among many, which may be used to illustrate this important aspect of the present invention, is a method for visualising a tetracysteine-tagged analyte molecule using a compound of formula I, wherein X is As, $Z^1$ together with $Z^2$ and $Z^3$ together with $Z^4$ both represent ethylene, $R^1$ is methoxy, $R^4$ is 4-fluorophenyl, and $R^2$, $R^3$, $R^5$, and $R^6$ all are hydrogen. Such a method provides for the unique opportunity of incorporating one of, for example, $^3H$, $^{11}C$, or $^{14}C$ in $R^1$, or $^{18}F$ in $R^4$, while retaining the same molecular structure, physical chemical properties, and binding affinity of the so prepared set of four distinctly labeled probes. Similarly, probes carrying iodine isotopes, e. g. in $R^4$, which may be for example iodophenyl, such as 4-iodophenyl, may be combined with constitutionally identical probes carrying $^3H$, $^{11}C$, or $^{14}C$ in $R^1$. As such, the method provided here finds broad application within the life sciences, including drug discovery and development, agricultural research, and molecular biology.

Accordingly, in one embodiment the method for visualizing a tetracysteine-tagged analyte molecule comprises a) contacting a first sample of said tetracysteine-tagged analyte molecule with a first compound of formula I to produce a first tetracysteine-tagged analyte molecule; and b) contacting a second sample of said tetracysteine-tagged analyte molecule with a second compound of formula I to produce a second tetracysteine-tagged analyte molecule; wherein said first and second compounds of formula I differ only in that they comprise a different isotope atom, and wherein said first and second tetracysteine-tagged analyte molecules are visualized by different techniques.

The invention also provides a kit comprising a first compound of formula I, and a second compound of formula I, wherein said first and second compounds of formula I differ only in that they comprise a different isotope atom. The invention also provides a kit comprising a first complex between a first compound of formula I, and a first sample of a tetra-cysteine tagged molecule; and a second complex between a second compound of formula I and a second sample of the tetra-cysteine tagged molecule, wherein said first and second compounds of formula I differ only in that they comprise a different isotope atom. The kits find use in the above methods.

The present inventors have shown experimentally, that the type of probes which are utilised in the method, i. e. compounds of the general formula I, similarly to known biarsenical compounds, show a high affinity for typical tetracysteine-tagged analyte molecules. Since not one radiolabeled biarsenical has previously been synthesised, issues related to radiolysis have not been addressed. It is generally true, that biarsenicals lacking the carboxylic acid in the $R^4$ group, which was always present in known fluorescent biarsenicals, but entirely unsuitable for the present invention, are as good as insoluble in organic solvents, making their preparation and purification very challenging.

In one embodiment of the method, the compound of formula I is typically mixed with the tagged analyte molecule of interest, and provided to a host, tissue, organ, matrix, cell culture, cell homogenate, or other target system of interest. Application according to the method may be through syringing, pipetting, soaking, immersing, or by other means known to the artisan.

Optionally, the method may include the addition of dithiol antidotes, which may be useful to minimise nonspecific binding or toxicity. Useful such dithiols include 1,2-dithiols such as ethanedithiol, 2,3-dimercaptopropanol, dithiothreitol, and the like.

The present invention provides a method for visualising, locating, measuring, or quantifying any tetracysteine-tagged analyte molecule provided that said analyte molecule comprises appropriately situated cysteine residues. For example it may comprise at least one amino acid sequence of the form -Cys-Cys-$X_{aa}$-$X_{aa}$-Cys-Cys-[SEQ ID NO 3], wherein each $X_{aa}$ represents any non-cysteine amino acid residue, including naturally occurring amino acid residues, unnatural amino acid residues, and other residues of the general formula —HN—$CA^1A^2$-CO—, where $A^1$ and $A^2$ are the same or different and represent any substituent. A preferred sequence is when -Cys-Cys-$X_{aa}$-$X_{aa}$-Cys-Cys- is -Cys-Cys-Pro-Gly-Cys-Cys- [SEQ ID NO 4]. Analyte molecules where the method is particularly useful include oligopeptides, proteins, glycoproteins, and antibodies.

Further advantages of the method provided herein include the application of well-established radiochemical methodology, both for preparing and purifying the biarsenical probe, and for visualising the tagged analyte by standard techniques. Additionally, for broadening the scope of the method even further, a variety of useful radiolabelled biarsenical probes may be designed, synthesised and tested first in a non-radiolabelled form, since analyte affinity or other relevant observations are directly transferable into the labeled species. Novel, non-isotope-labeled compounds (for example non-radiolabeled compounds) of formula I are consequently also a part of the present invention.

In addition to the method which employs radiolabeled versions of the compounds of formula I, the inventors have appreciated that there are applications of the method in which the label is a non-radioactive (i. e. stable) isotope, such as one or more atoms of $^2H$, $^{19}F$ or $^{13}C$. Such variations of the method are also included in the scope of the present invention. In cases where the compound of formula I comprises one or more of e. g. the stable isotopes $^2H$ and $^{13}C$, this invention intends to provide, at each labeled site, levels of the isotope well above those usually present due to natural isotope abundance. For example, any compound of formula I carrying the $^{13}C$ label, should preferably have a level of this isotope, at each labeled position in the case where multiple labels are incorporated, above 2%, typically above 50%, preferably above 80%, and ideally above 90%. Analogous, but not necessarily identical, levels apply in the case of $^2H$ and $^{19}F$.

Preferred embodiments of the second aspect of the present invention are those methods for visualising a tetracysteine-tagged analyte molecule which comprise contacting said tetracysteine-tagged analyte molecule with a preferred compound of formula I, as defined in any of the preferred embodiments detailed above.

Further preferred embodiments of the method disclosed herein include the method wherein the tetracysteine-tagged analyte molecule comprises at least one amino acid sequence of the form -Cys-Cys-$X_{aa}X_{aa}$-Cys-Cys- [SEQ ID NO 3], wherein each $X_{aa}$ represents a non-cysteine amino acid residue. In alternative embodiments, the sequence includes one, three, four or five $X_{aa}$ groups between the two pairs of Cys residues [SEQ ID NO 3].

Typical embodiments are those wherein $X_{aa}$ represents any non-cysteine amino acid residue, including naturally occurring amino acid residues, unnatural amino acid residues, and other residues of the general formula —HN—$CA^1A^2$-CO—, where $A^1$ and $A^2$ are the same or different and represent any substituent.

A preferred sequence is when the tetracysteine-tagged analyte molecule contains the sequence -Cys-Cys-Pro-Gly-Cys-Cys- [SEQ ID NO 4].

In the method, it is preferred that the compound of formula I is visualised by in vitro autoradiography, in vivo PET, in vivo SPECT or in vivo MRI. It is further preferred that the analyte molecule is an oligopeptide, a protein, a glycoprotein, or an antibody. Especially preferred analytes include proteins and antibodies, particularly proteins.

Additionally, the method according to the present invention is particularly characterised in that the compound of formula I and the tetracysteine-tagged analyte molecule are premixed prior to administration into the matrix where visualisation is desired.

Visualisation according to the herein disclosed method is especially efficient when any one relevant isotope, including, but not limited to, e. g. $^3H$, $^{11}C$, $^{14}C$, $^{18}F$, may be deliberately incorporated into a single, structurally distinct probe, i. e. a compound of formula I.

Optionally, the method may comprise the additional step of converting a suitable precursor to the compound of formula I into the labeled probe, e. g. by incorporating the isotope atom (for example the radioactive atom) or group by means of synthesis. Optionally, the so obtained probe may be purified by standard techniques known to the skilled person.

The present invention includes a kit, comprising a precursor molecule that can be converted into a compound of formula I and one or more of: instructions for converting the precursor into a compound of formula I, reagents, handling instructions, safety information, and scientific background material. Preferably a kit comprises a precursor to a preferred compound of formula I, as defined above. For example a kit may comprise a compound of formula II, IIA, III or IIIA as defined below. The remaining components of the kit preferably allow the visualisation of a preferred analyte molecule, as defined above.

The present invention also provides flexible synthetic approaches to a series of molecular probes containing any of a number of isotope atoms (e.g. radioisotope atoms). Controlled introduction of groups containing any of a variety of isotope atoms on to the same xanthene scaffold/structure is provided by the synthetic methods of the invention. This enables translation of results between matrices, e. g. in vitro autoradiography, in vivo PET, in vivo SPECT or in vivo MRI, using multiple differently labeled probes of the same exact chemical constitution.

In a fourth aspect, the present invention provides methods for synthesising a compound of formula I, as defined above, comprising the steps of 1) reacting a suitable precursor molecule with a reagent capable of introducing an isotope (for example radioactive) atom or group, and, optionally 2) purifying and isolating the so obtained compound of formula I.

Examples of suitable precursor molecules include compounds of formula II:

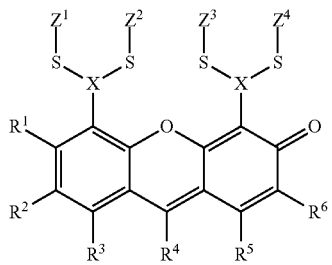

wherein

X is P or, more preferably, As;

$Z^1$-$Z^4$ are independently $C_1$-$C_6$ alkyl, or $Z^1$ and $Z^2$ or $Z^3$ and $Z^4$, or both, together form an ethylene or propylene chain, which may optionally be substituted;

one of $R^1$-$R^6$ is an OH, SH or $NH_2$ group; and the remainder of $R^1$-$R^6$ are independently selected from the group comprising hydrogen, optionally substituted $C_1$-$C_6$ alkyl, optionally substituted $C_6$-$C_{10}$ aryl, optionally substituted $C_1$-$C_6$ acyl, optionally substituted $C_6$-$C_{10}$ aroyl, optionally substituted $C_1$-$C_6$ alkoxy, optionally substituted $C_6$-$C_{10}$ aryloxy, optionally substituted mono- or di- $C_1$-$C_6$ alkyl amino, optionally substituted mono- or di- $C_6$-$C_{10}$ arylamino, optionally substituted $C_1$-$C_6$ alkylthio, optionally substituted $C_6$-$C_{10}$ arylthio, halogen, hydroxy, formyl, cyano, —$CONH_2$, —$CONH(C_1$-$C_6$ alkyl), —$CON(C_1$-$C_6$ alkyl)$_2$, —$NHCO(C_1$-$C_6$ alkyl).

Such precursors may be reacted with alkylating agents carrying at least one isotope (for example radioactive) atom. Useful reagents are those containing at least one of $^3$H, $^{11}$C, or $^{14}$C, and further a nucleophuge which may be substituted by an aryloxy, arylthio, or arylamino group. Particularly useful reagents include $C_1$-$C_6$ alkyl halides and sulfonates, triflates, tosylates, mesylates, brosylates, nosylates, which may carry one or more $^3$H, $^{11}$C, or $^{14}$C atoms. In the art, reagents such as $^3H_nH_{3-n}$C—X, wherein X is a nucleophuge such as a halide or a sulfonate, triflate, tosylate, mesylate, brosylate, or nosylate, and n is 1, 2, or 3, are known, as are the analogous $^2H_nH_{3-n}$C—X reagents. Similarly, reagents such as $H_3^{13}$C—X, $H_3^{14}$C—X, $H_3^{11}$C—X, where X is a nucleophuge as defined above are available. A preferred form of $^3H_nH_{3-n}$C—X is $^3H_3$C—X.

Further suitable precursor molecules include compounds of formula III:

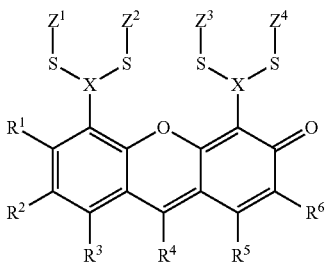

wherein

X is P or, more preferably, As;

$Z^1$-$Z^4$ are independently $C_1$-$C_6$ alkyl, or $Z^1$ and $Z^2$ or $Z^3$ and $Z^4$, or both, together form an ethylene or propylene chain, which may optionally be substituted, $R^4$ is phenyl substituted with a trimethylammonium group, a halogen or a nitro group; and the remainder of $R^1$-$R^6$ are independently selected from the group comprising hydrogen, optionally substituted $C_1$-$C_6$ alkyl, optionally substituted $C_6$-$C_{10}$ aryl, optionally substituted $C_1$-$C_6$ acyl, optionally substituted $C_6$-$C_{10}$ aroyl, optionally substituted $C_1$-$C_6$ alkoxy, optionally substituted $C_6$-$C_{10}$ aryloxy, optionally substituted mono or di- $C_1$-$C_6$ alkyl amino, optionally substituted mono or di- $C_6$-$C_{10}$ arylamino, optionally substituted $C_1$-$C_6$ alkylthio, optionally substituted $C_6$-$C_{10}$ arylthio, halogen, hydroxy, formyl, amino, cyano, —$CONH_2$, —$CONH(C_1$-$C_6$ alkyl), —$CON(C_1$-$C_6$ alkyl)$_2$, —$NHCO(C_1$-$C_6$ alkyl).

In such precursor molecules, $R^4$ carries a group which allows substitution, for example by nucleophilic aromatic substitution, for example by isotopes of fluoride or iodide. Such precursors may for example be reacted with radioactive fluorine reagents to provide $^{18}$F labeled compounds of formula I, or with $^{19}$F-containing reagents to provide $^{19}$F-labeled compounds of formula I.

The present invention further provides methods for synthesising a compound of formula I, wherein the compound of formula I is a preferred compound of formula I, as defined herein above. The method may comprise one or both steps of reacting a suitable precursor molecule with a reagent capable of introducing a radioactive atom or group, and, optionally, purifying and isolating the so obtained compound of formula I. It is generally preferred that both steps are incorporated in the method of synthesis.

Preferred precursor molecules, relevant to the method of synthesis incorporated herein, are those compounds according to formula II, and preferred embodiments as presented above, wherein $R^1$ is a phenolic group, i. e. HO—. Such precursors may be reacted with alkylating agents carrying at least one isotope (for example radioactive) atom. Useful reagents are those containing at least one of $^3$H, $^{11}$C, or $^{14}$C, and further a nucleophuge which may be substituted by an aryloxy group. Particularly useful reagents include $C_1$-$C_6$ alkyl halides and triflates, tosylates, mesylates, brosylates, nosylates, which may carry one or more $^3$H, $^{11}$C, or $^{14}$C atoms. In the art, reagents such as $^3H_nH_{3-n}$C—X, where X is a nucleophuge such as a halide or sulfonate, and n is 1, 2, or 3, are known, as are the analogous $^2H_nH_{3-n}$C—reagents. Similarly, reagents such as $H_3^{13}$C—X, $H_3^{14}$C—X, $H_3^{11}$C—X, where X is a nucleophuge such a halide or sulfonate are available.

Further preferred suitable precursor molecules include compounds of formula III, wherein $R^4$ is a phenyl group which carries a trimethylammonium, a bromo, an iodo, or a nitro substituent, preferably in the 4-position of the phenyl group. Such precursors may be reacted with radioactive fluorine reagents via nucleophilic aromatic substitution, for example by use of K[$^{18}$F]—K$_{222}$ in a suitable solvent such as DMSO under microwave irradiation as described in Karramkam, M. et al. *J. Labelled Compd. Rad.* 2003, 46, 979 and in WO2007/020400.

Reagents containing the positron emitting isotopes, $^{11}$C and $^{18}$F, may be generated in a cyclotron, followed by trapping by a suitable methods, and optionally further synthetic steps to provide the desired reagent. The generation and further manipulation of labeled reagents and intermediates, and their use in the synthesis of more complex targets, is well known to the one skilled in the art of radiochemistry and has been reviewed e. g. in Långström et al. *Acta Chem. Scand.* 1999, 53, 651). For additional references, see e. g. Ali et al. *Synthesis* 1996, 423, Antoni G., Kihlberg T., and Långström B. (2003) Handbook of nuclear chemistry, edited by Vertes A., Nagy S., and Klenscar Z., Vol. 4, 119-165, Saljoughian et al. *Synthesis* 2002, 1781, or McCarthy et al. *Curr. Pharm. Des.* 2000, 6, 1057.

The invention also provides a method for synthesising a compound of formula I comprising the steps of a1) reacting a compound of formula IIA

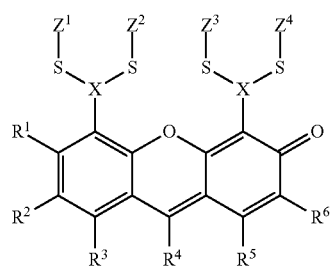

IIA wherein

X is As or P;

$Z^1$-$Z^4$ are independently lower alkyl, or $Z^1$ and $Z^2$ or $Z^3$ and $Z^4$, or both, together form an ethylene or propylene chain, which alkyl, ethylene or propylene chain may optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl);

$R^1$ is hydroxy;

$R^4$ is selected from the group consisting of hydrogen, halogen, hydroxy, formyl, cyano, —$CONH_2$, —$CONH(C_1$-$C_6$ alkyl), —$CON(C_1$-$C_6$ alkyl)$_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkyl amino, mono or di- $C_6$-$C_{10}$ arylamino, $C_1$-$C_6$ alkylthio, $C_6$-$C_{10}$ arylthio, halogen, hydroxy, formyl, cyano, —$CONH_2$, —$CONH(C_1$-$C_6$ alkyl), —$CON(C_1$-$C_6$ alkyl)$_2$, and —$NHCO(C_1$-$C_6$ alkyl); and $R^2$, $R^3$, $R^5$ and $R^6$ are each independently selected from the group consisting of hydrogen, halogen, formyl, cyano, —$CONH_2$, —$CONH(C_1$-$C_6$ alkyl), —$CON(C_1$-$C_6$ alkyl)$_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl);

with a $C_1$-$C_6$ alkyl group which comprises a leaving group and at least one isotope atom;

or a2) reacting a compound of formula IIIA

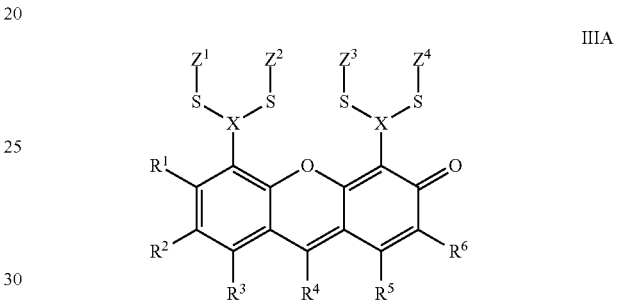

IIIA wherein

X is As or P;

$Z^1$-$Z^4$ are independently lower alkyl, or $Z^1$ and $Z^2$ or $Z^3$ and $Z^4$, or both, together form an ethylene or propylene chain, which alkyl, ethylene or propylene chain may optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl); and $R^1$ is selected from the group consisting of hydrogen, halogen, hydroxy, formyl, cyano, —$CONH_2$, —$CONH(C_1$-$C_6$ alkyl), —$CON(C_1$-$C_6$ alkyl)$_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkylamino, mono or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono or di- $C_1$-$C_6$ alkyl amino, mono or di- $C_6$-$C_{10}$ arylamino, $C_1$-$C_6$ alkylthio, $C_6$-$C_{10}$ arylthio, halogen, hydroxy, formyl, cyano, —$CONH_2$, —$CONH(C_1$-$C_6$ alkyl), —$CON(C_1$-$C_6$ alkyl)$_2$, and —$NHCO(C_1$-$C_6$ alkyl);

$R^4$ is phenyl substituted with a leaving group; and $R^2$, $R^3$, $R^5$ and $R^6$ are independently selected from the group consisting of hydrogen, halogen, formyl, cyano, —CONH$_2$, —CONH(C$_1$-C$_6$ alkyl), —CON(C$_1$-C$_6$ alkyl)$_2$, —NHCO(C$_1$-C$_6$ alkyl), C$_1$-C$_6$ alkyl optionally substituted by one or more halogens, C$_2$-C$_6$ alkenyl, C$_2$-C$_4$ alkynyl, C$_6$-C$_{10}$ aryl, C$_6$-C$_{10}$ heteroaryl, C$_1$-C$_6$ acyl, C$_6$-C$_{10}$ aroyl, C$_1$-C$_6$ alkoxy, C$_6$-C$_{10}$ aryloxy, di- C$_1$-C$_6$ alkylamino, di- C$_6$-C$_{10}$ arylamino, C$_1$-C$_6$ alkylthio and C$_6$-C$_{10}$ arylthio, wherein said C$_1$-C$_6$ alkyl, C$_6$-C$_{10}$ aryl, C$_6$-C$_{10}$ heteroaryl, C$_1$-C$_6$ acyl, C$_6$-C$_{10}$ aroyl, C$_1$-C$_6$ alkoxy, C$_6$-C$_{10}$ aryloxy, di- C$_1$-C$_6$ alkylamino, di- C$_6$-C$_{10}$ arylamino, C$_1$-C$_6$ alkylthio and C$_6$-C$_{10}$ arylthio may each optionally be substituted by one or more substituents independently selected from the group consisting of C$_1$-C$_6$ alkyl optionally substituted by one or more halogens, C$_2$-C$_6$ alkenyl, C$_2$-C$_4$ alkynyl, C$_6$-C$_{10}$ aryl, C$_1$-C$_6$ acyl, C$_6$-C$_{10}$ aroyl, C$_1$-C$_6$ alkoxy, C$_6$-C$_{10}$ aryloxy, di- C$_1$-C$_6$ alkyl amino, di- C$_6$-C$_{10}$ arylamino, C$_1$-C$_6$ alkylthio, C$_6$-C$_{10}$ arylthio, halogen, formyl, cyano, —CONH$_2$, —CONH(C$_1$-C$_6$ alkyl), —CON(C$_1$-C$_6$ alkyl)$_2$, and —NHCO(C$_1$-C$_6$ alkyl);

with an isotopic fluorine reagent;
and, optionally
b) purifying the so obtained compound of formula I by chromatography,
and, optionally
c) dissolving or diluting the so purified compound of formula I with a solvent.

Suitable leaving groups include halides, sulfonates, triflates, tosylates, mesylates, brosylates, nosylates, nitro groups and trialkylammonium groups (e.g. trimethylammonium). In the case of a phenyl group substituted with a leaving group, the leaving group is preferably halide, a nitro group or a trialkylammonium group (e.g. trimethylammonium). In the case of a C$_{1-6}$alkyl group which comprises a leaving group, the leaving group is preferably halide, sulfonate, triflate, tosylate, mesylate, brosylate or nosylates.

Suitable isotopic fluoride reagents are known in the art, and include K[$^{18}$F]—K$_{222}$.

Also provided are compounds of formula II, IIA, III and IIIA as defined above. Such compounds are useful intermediates for the synthesis of the compounds of the invention. For example, an intermediate may be reacted with suitable groups containing different isotope atoms (e.g. radioisotope atoms) to produce first and second compounds of formula I which, other than possessing different isotope atoms, have the same chemical constitution. As a result, the same probe (i. e. of identical constitution except for the presence of different isotope atoms) may be applied in a whole range of studies, involving e. g. studies performed in vitro, such as on cells, organelles, tissues, or any other relevant matrix, and studies performed in vivo, such as in microbes, whole animals, or humans. Preferences for the substituents X, Z$^1$ to Z$^4$, and R$^1$ to R$^6$ in the compounds of formula II, IIA, III and IIIA are as described above for the compounds of formula I.

The invention also provides a method for synthesising a compound of formula I, comprising the steps of
a1) introducing at least one radioactive atom, selected from the group consisting of $^{11}$C, $^{18}$F, $^{75}$Br, $^{76}$Br, $^{120}$I, $^{123}$I, $^{125}$I, $^{131}$I, $^3$H, and $^{14}$C, in R$^1$ via alkylation of a compound of formula I wherein R$^1$ is hydroxy, or
a2) introducing at least one radioactive atom, selected from the group consisting of $^{11}$C, $^{18}$F, $^{75}$Br, $^{76}$Br, $^{120}$I, $^{123}$I, $^{125}$I, $^{131}$I, $^3$H, and $^{14}$C, in R$^4$ via substitution of a compound of formula I wherein R$^4$ comprises a leaving group selected from —NO$_2$, —Br, —I, and N$^+$Me$_3$, and, optionally
b) purifying the so obtained compound of formula I by chromatography,
and, optionally
c) dissolving or diluting the so purified compound of formula I with a solvent suitable for the intended use.

Routes for the general assembly of xanthene precursors useful for synthesising a compound of formula I, II, IIA, III or IIIA are known in the art, for example in Yang et. al. *J. Org. Chem.* 2005, 70, 6907-6912, and references cited therein. Nonlimiting examples of the preparation of relevant precursors, and their conversion into useful compounds of formula I, II, IIA, III or IIIA are included in the working examples herein.

In a fifth aspect, this invention provides non-labeled novel compounds of formula I, useful as reference substances within radiochemical research and development relevant to biarsenical probes. In particular, compounds of general formula I, wherein R$^2$ is methoxy and/or R$^4$ is 4-fluorophenyl are useful.

Also provided are non-labeled novel compounds of formula I, useful as reference substances within radiochemical research and development relevant to biarsenical probes, which include compounds of general formula I, wherein R$^2$ is methoxy or R$^4$ is 4-fluorophenyl. It is preferred, within this embodiment, that at least two, such as three, and preferably all, of R$^2$, R$^3$, R$^5$, and R$^6$ are hydrogen. Further preferred are compounds of formula I wherein R$^2$ is methoxy, R$^4$ is 4-fluorophenyl, and least two, such as three, and preferably all, of R$^2$, R$^3$, R$^5$, and R$^6$ are hydrogen.

Preferred non-labeled compounds include those wherein R$^1$ is C$_1$-C$_6$ alkoxy, for example methoxy, and R$^4$ is fluorophenyl, for example 4-fluorophenyl, and at least three, and preferably all, of R$^2$, R$^3$, R$^5$, and R$^6$ are hydrogen. Further preferred are non-labeled compounds wherein Z$^1$ and Z$^2$ together represent alkylene, such as ethylene, and wherein Z$^3$ and Z$^4$ together represent alkylene, such as ethylene, and X is As.

In a sixth aspect, the present invention provides a complex between a tetracysteine-tagged analyte molecule, as defined above, and a compound of formula I, as defined above.

Such complex is characterised by a high binding affinity, through the multiple As/P—S interactions, and may be isolated and characterised by methods known in the art, for example NMR, radiodetection or mass spectroscopy.

A complex according to the present invention is of a preferred constitution when the complex contains a tetracysteine-tagged analyte molecule, as defined above, including preferred such analyte molecules defined above, and comprises a preferred compound of formula I, as defined herein above.

The invention detailed herein further provides the use of a compound according to formula I for visualising a tetracysteine-tagged analyte molecule. Preferred embodiments in this context utilise a preferred compound of formula I, as defined above, or a preferred analyte molecule, as defined above, a preferred complex, as defined above, or a combination of preferred embodiments, as detailed above.

In a seventh aspect, the present invention provides a method for the treatment or prophylaxis of cancer or other hyperproliferative disorder in a mammal, which comprises administering to the mammal a therapeutically effective amount of a compound of formula I as defined above, wherein at least one of R$^1$-R$^6$ comprises a radioactive isotope atom. In this aspect, it is preferred that the compound of formula I is provided as a complex with a tetracysteine-tagged biomolecule.

The method allows for targeted radiotherapy, utilizing a compound of formula I carrying a suitable radioisotope capable of producing irradiation of adequate nature and intensity to affect cells, for example tumor cells or other malignant or otherwise diseaseassociated cells, in such a way as to provide treatment for a mammal, for example a human, in need thereof. The compound of formula I may, in the method for targeted radiotherapy, be provided as a complex with a suitable targeting entity, such as for example an antibody or other protein with affinity for the target cell or tissue, by way of a suitable tag, such as a tetracysteine tag.

The present invention also provides a compound of formula I as defined above, wherein at least one of $R^1$-$R^6$ comprises a radioactive isotope atom, for use as a medicament, for example in the treatment or prophylaxis of cancer or other hyperproliferative disorder. The present invention also provides a pharmaceutical composition which comprises a compound of formula I as defined above, wherein at least one of $R^1$-$R^6$ comprises a radioactive isotope atom, together with a pharmaceutically acceptable carrier.

EXAMPLES

Example 1

Synthesis of Compounds of Formula I

General

Commercial reagents were used as received. Full assignment of 1H and 13C chemical shifts are based on the 1D and 2D FT NMR spectra on a Bruker Avance III 400 MHz instrument. Solvent peaks in $^{13}$C— and $^1$H-NMR were used as chemical shift references. All reactions sensitive to moisture or oxygen were carried out under Ar atmosphere in flame-dried glassware. THF was distilled over potassium and $CH_2Cl_2$ was distilled over $CaH_2$ prior to use.

Synthesis of 2,5-di-(1,3,2-dithiarsolan-2-yl)-9-(4-fluorophenyl)-6-hydroxy-3-fluorone Bis(2,4-dimethoxyphenyl)-4-fluorophenylmethanol (PSMXB-8)

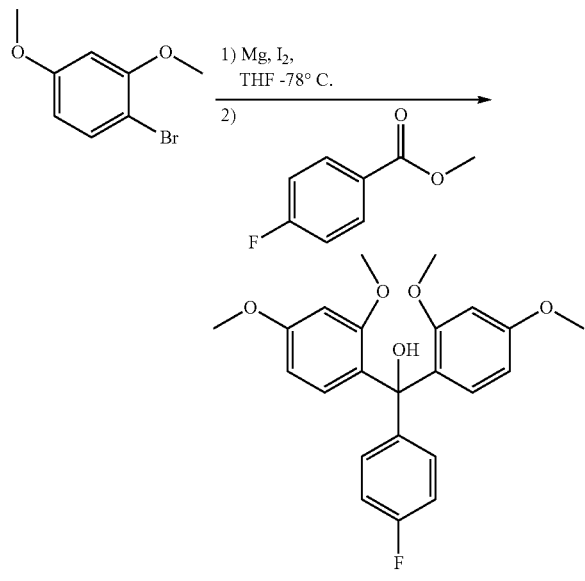

Magnesium turnings (6.923 g, 285 mmol) and a few crystals of $I_2$ were placed in a 1-L three-neck round-bottom flask fitted with a dropping funnel and a condenser. A solution of 2,4-dimethoxybromobenzene (42.7 mL, 294 mmol) in 60 mL of anhydrous THF was added dropwise to the magnesium. Additional THF (~300 mL) was added by portion to cool the reaction. The mixture was stirred for 30 min. The resulting Grignard reagent (2,4-dimethoxyphenylmagnesium bromide) was cooled in a dry ice/acetone bath before a solution of 4-fluoro methyl benzoate (15.5 mL, 120 mmol) in 110 mL of dry THF was added dropwise. The mixture was stirred overnight and then quenched with 1 L of distilled water and neutralised with 2 N HCl. The resulting green mixture was extracted with ethyl acetate (3×300 mL). The combined extracts were dried over MgSO4, filtered, and evaporated to dryness. The residue was purified by precipitation using EtOAc and heptane to afford an off-white solid (37 g, 77%).

$^1$H NMR (400 MHz, CDCl3) δ 7.27-7.18 (m, J=8.4, 5.7 Hz, 2H), 7.00-6.81 (m, 4H), 6.50 (d, J=2.0 Hz, 2H), 6.40 (dd, J=8.6, 2.1 Hz, 2H), 5.12 (s, 1H), 3.80 (s, 6H), 3.54 (s, 6H). $^{13}$C NMR (101 MHz, CDCl$_3$) δ 161.64 (d, J=244.2 Hz), 143.29 (d, J=3.2 Hz), 129.45 (d, J=7.9 Hz), 113.86 (d, J=21.1 Hz).

In analogy with the example above, the following intermediates are prepared: bis(2,4-dimethoxyphenyl)-4-bromoophenylmethanol, bis(2,4-dimethoxyphenyl)-4-iodophenylmethanol, bis(2,4-dimethoxyphenyl)-4-nitrophenylmethanol.

9-(4-fluorophenyl)-6-methoxy-3-fluorone (PSMXB-2)

PSMXB-8 obtained as above was dissolved in dichloromethane and treated with six molar equivalents of $BBr_3$ at −78° C. until TLC indicated complete conversion. The resulting solution was allowed to reach room temperature, quenched with water, and extracted with ethyl acetate. The organic phases were then combined, dried over sodium sulfate, and evaporated to dryness. Purification of the resulting crude product by silica gel chromatography (ethyl acetate) provided a poorly soluble solid, which was used without further purification. LC-MS showed the expected molecular ion at m/z 321 [M+1]$^+$.

9-(4-fluorophenyl)-6-hydroxy-3-fluorone (PSMXB-1)

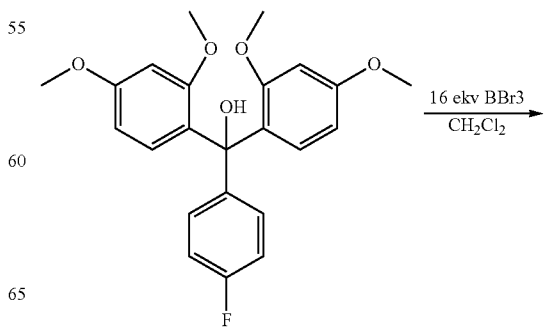

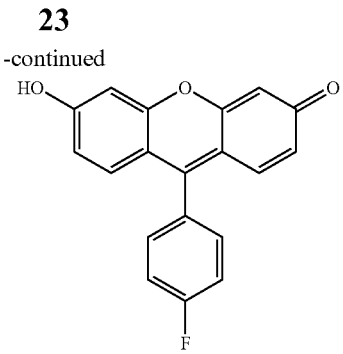

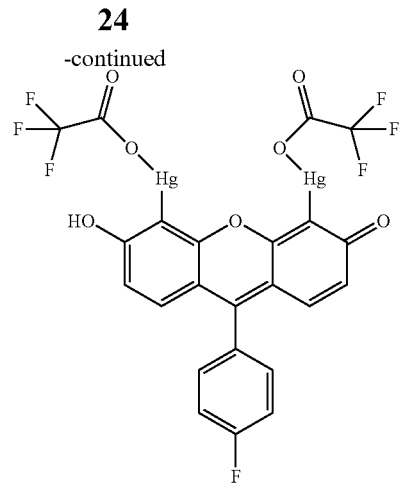

A solution of bis(2,4-dimethoxyphenyl)-4-fluorophenyl-methanol (17 g, 42.7 mmol) in 500 mL of dry $CH_2Cl_2$ was cooled to −78° C. using a dry ice/EtOH bath before $BBr_3$ (66 mL, 683 mmol) was added over 40 minutes. The mixture was allowed to warm to room temperature gradually and stirred overnight. The reaction mixture was transferred into a 2 L of cold water using cannula. The layers were separated and water was extracted with $CH_2Cl_2$ (2×400 mL) and EtOAc (5×400 mL). The red precipitate was filtered off and discarded. The combined extracts were dried over $Na_2SO_4$ and filtered and concentrated. The residue was purified by precipitation using methanol and EtOAc to afford mustard-coloured powder (2.38 g, 18%).

1H NMR (400 MHz, MeOD) δ 7.81 (d, J=9.3 Hz, 2H), 7.69-7.64 (m, 2H), 7.55-7.48 (m, 2H), 7.39 (d, J=2.3 Hz, 2H), 7.30 (dd, J=9.3, 2.3 Hz, 2H).

Similarly, using the above defined conditions, applying a suitable excess of $BBr_3$ at −78° C. until TLC indicates complete conversion, the intermediates bis(2,4-dimethoxyphenyl)-4-bromoophenylmethanol, bis(2,4-dimethoxyphenyl)-4-iodophenylmethanol, bis(2,4-dimethoxyphenyl)-4-nitrophenylmethanol are converted into the corresponding fluorones, i. e. 9-(4-bromophenyl)-6-methoxy-3-fluorone, 9-(4-iodophenyl)-6-methoxy-3-fluorone, 9-(4-nitrophenyl)-6-methoxy-3-fluorone.

9-(4-fluorophenyl)-6-hydroxy-3-fluorone-2,5-dimercuric trifluoroacetate (PSMXB-3)

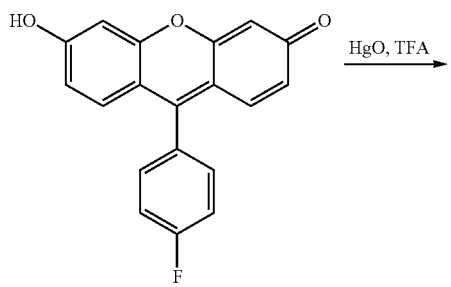

HgO (2.77 g, 12.8 mmol) was dissolved in 30 ml of trifluoroacetic acid, 9-(4-fluorophenyl)-6-hydroxy-3-fluorone (1.95 g, 6.39 mmol) was added and the mixture was stirred overnight. The TFA was evaporated and 50 mL of water was added. The product was filtered off and washed with 3 portions of water. The product was dried using high vacuum pump to yield orange solid (5.06 g, 85%).

1H NMR (400 MHz, DMSO+TFA) δ 7.74-7.66 (m, 2H), 7.61-7.54 (m, 4H), 7.31 (d, J=9.1 Hz, 2H).

9-(4-fluorophenyl)-6-methoxy-3-fluorone-2,5-dimercuric trifluoroacetate (PSMXB-5)

To a solution of 40 mg (0.19 mmol) mercuric oxide in 2 mL of trifluoroacetic acid was added 30 mg (0.095 mmol) of PSMXB-2, and the mixture was stirred over night at room temperature. The trifluoroacteic acid was remowed, and the residue triturated twice with 3 mL of water. Drying in vacuo returned 70 mg (78%) of a deep red powder.

The intermediates 9-(4-bromophenyl)-6-methoxy-3-fluorone-2,5-dimercuric trifluoroacetate, 9-(4-iodophenyl)-6-methoxy-3-fluorone-2,5-dimercuric trifluoroacetate, 9-(4-nitrophenyl)-6-methoxy-3-fluorone-2,5-dimercuric trifluoroacetate are prepared in analogy with the example provided above.

2-(1,3,2-Dithiarsolan-2-yl)-9(4-fluorophenyl)-6-methoxy-3-fluorone (PSMXB-7)

To a solution of 70 mg (0.074 mmol) PSMXB-5 in 1 mL of dry NMP there was added 120 microlitres (1.47 mmol) arsenic trichloride, 100 microlitres of diisopropyl amine, and 5 mg $Pd(OAc)_2$. The reaction mixture was magnetically stirred under argon over night, and then transferred into 30 mL of a 1:1 mixture of 0.2 M $KH_2PO_4$ (aq) pH 7 buffer and acetone. Extraction with $CHCl_3$, drying over sodium sulfate, removal of solvent, and finally purification by gradient silica gel chromatography (neat toluene to toluene/ethyl acetate 4:1) gave PSMXB-7. The material displayed the expected MS and NMR spectra.

Analogously, 9-(4-bromophenyl)-6-methoxy-3-fluorone-2,5-dimercuric trifluoroacetate, 9-(4-iodophenyl)-6-methoxy-3-fluorone-2,5-dimercuric trifluoroacetate, and 9-(4-nitrophenyl)-6-methoxy-3-fluorone-2,5-dimercuric trifluoroacetate provide the corresponding compounds of formula I, i. e. 2(1,3,2-dithiarsolan-2yl)-9(4-bromophenyl)-6-methoxy-3-fluorone, 2(1,3,2-dithiarsolan-2yl)-9(4-iodophenyl)-6-methoxy-3-fluorone, and 2-(1,3,2-dithiarsolan-2yl)-9 (4-nitrophenyl)-6-methoxy-3-fluorone.

The latter is optionally transformed into the precursor carrying a 4-trimethylammonium phenyl group at $R^4$ by reduction with either dithionite in EtOH or catalytic hydrogenation, followed by exhaustive methylation with methyl triflate.

2,5-di-(1,3,2-dithiarsolan-2-yl)-9-(4-fluorophenyl)-6-hydroxy-3-fluorone (PSMXB-4)

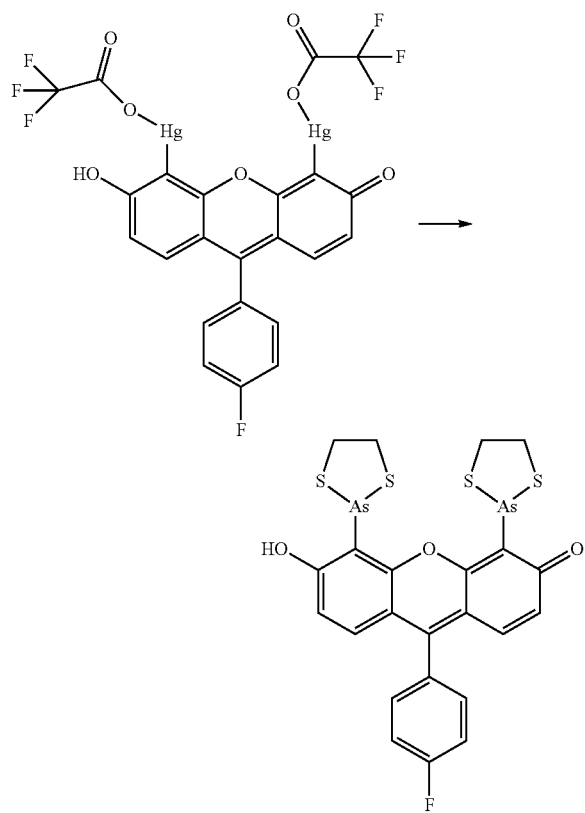

The 9-(4-fluorophenyl)-6-hydroxy-3-fluorone-2,5-dimercuric trifluoroacetate (5.0 g, 5.37 mmol) was dissolved in 53 mL of dry N-methylpyrrolidone under argon atmosphere, $AsCl_3$ (9.0 mL, 107 mmol) and N,N-diisopropylethylamine (7.5 mL, 43.0 mmol) were added via syringe. 32 mg of palladium (II) acetate was added and the mixture was stirred at 55° C. for two hours and then at room temperature overnight. The reaction mixture was transferred into a 500-mL Erlenmeyer flask containing well-stirred 320 mL of 1:1 vol/vol 0.3 M potassium phosphate buffer at pH 6.9 and acetone. 21 mL of 1,2-ethanedithiol was added to the solution and stirred for 30 minutes, and then 100 mL of chloroform was added and stirred for additional 20 minutes. The organic phase was separated and the water was extracted 3 times with chloroform, the combined organic layers were washed with water and dried over $Na_2SO_4$, filtered and concentrated. Methanol was added, large amount of white precipitate was formed, also a small amount of dark red liquid at the bottom of the flask. The precipitate was decanted, the remaining red liquid was dissolved in chloroform and collected. This procedure was repeated three times. The combined crude product was concentrated and purified by column chromatography using neat toluene to toluene:acetone 50:4 to yield a orange-red solid (1.0 g, 31%).

1H NMR (400 MHz, CDCl3) δ 10.57 (s, 1H), 7.41-7.21 (m, 2H), 7.08-6.97 (m, 1H), 6.62 (broad s, 1H), 3.88-3.27 (broad m, 1H).

The synthesis of compounds with similar structures are described in JOC 2005, 70, 6907; JACS 2008, 30, 8596, and Nature Protocols 2008, 3, 1527.

2,5-di-(1,3,2-Dithiarsolan-2yl)-9(4-fluorophenyl)-6-methoxy-3-fluorone (PSMXB-6)

To a solution of 5 mg (7.8 micromol) PSMXB-4 in 1 mL of dry DMF there was introduced two equivalents of methyl iodide and the mixture was stirred over night. The crude was purified by HPLC (Chromasil 100-5-C18 column 250×10 mm) using 80% acetonitrile in 50 mM ammonium acetate at 2.0 mL/min as the eluent ($t_R$ 21.7 minutes). The so obtained PSMXB-6 was pure according to LC-MS (m/z 653 [M+1]$^+$) and NMR.

2,5-di-(1,3,2-Dithiarsolan-2yl)-9(4-fluorophenyl)-6-[$^{13}C^2H_3$]methoxy-3-fluorone (6-[$^{13}C^2H_3$] PSMXB-6)

To a solution of 1 mg (1.56 micromol) PSMXB-4 in 0.5 mL of dry DMF was added two equivalents of [$^{13}C^2H_3$] methyl iodide and the mixture was left to stir over night at room temperature. The crude mixture was purified by HPLC (Chromasil 100-5-C18 column 250×10 mm) using 80% acetonitrile in 50 mM ammonium acetate at 2.0 mL/min as the eluent ($t_R$ 21.7 minutes). Analyses were consistent with pure $^{13}C^2H_3$ PSMXB-6 (LC-MS m/z 657 [M+1]$^+$; H-NMR displayed the expected peak pattern).

2,5-di-(1,3,2-Dithiarsolan-2yl)-9(4-fluorophenyl)-6-[$^{14}C$]methoxy-3-fluorone (6-[$^{14}C$] PSMXB-6).

To a solution of 31.9 mg (0.05 mmol) PSMXB-4 in 0.4 mL of dry DMF was added one tenth of an equivalent of [$^{14}C$] methyl iodide and the mixture was left to stir over night at room temperature. The crude mixture was then purified by HPLC (Chromasil 100-5-C18 column 250×10 mm) using 80% acetonitrile in 50 mM ammonium acetate at 2.0 mL/min as the eluent ($t_R$ 21.7 minutes). Analyses were consistent with pure [$^{14}C$] PSMXB-6 (LC-MS m/z 655 [M+1]$^+$; NMR displays the expected peak pattern).

2,5-di-(1,3,2-Dithiarsolan-2yl)-9(4-fluorophenyl)-6-[$^3H_3$]methoxy-3-fluorone (6-[$^3H_3$CO]-PSMXB-6).

Figure 4:
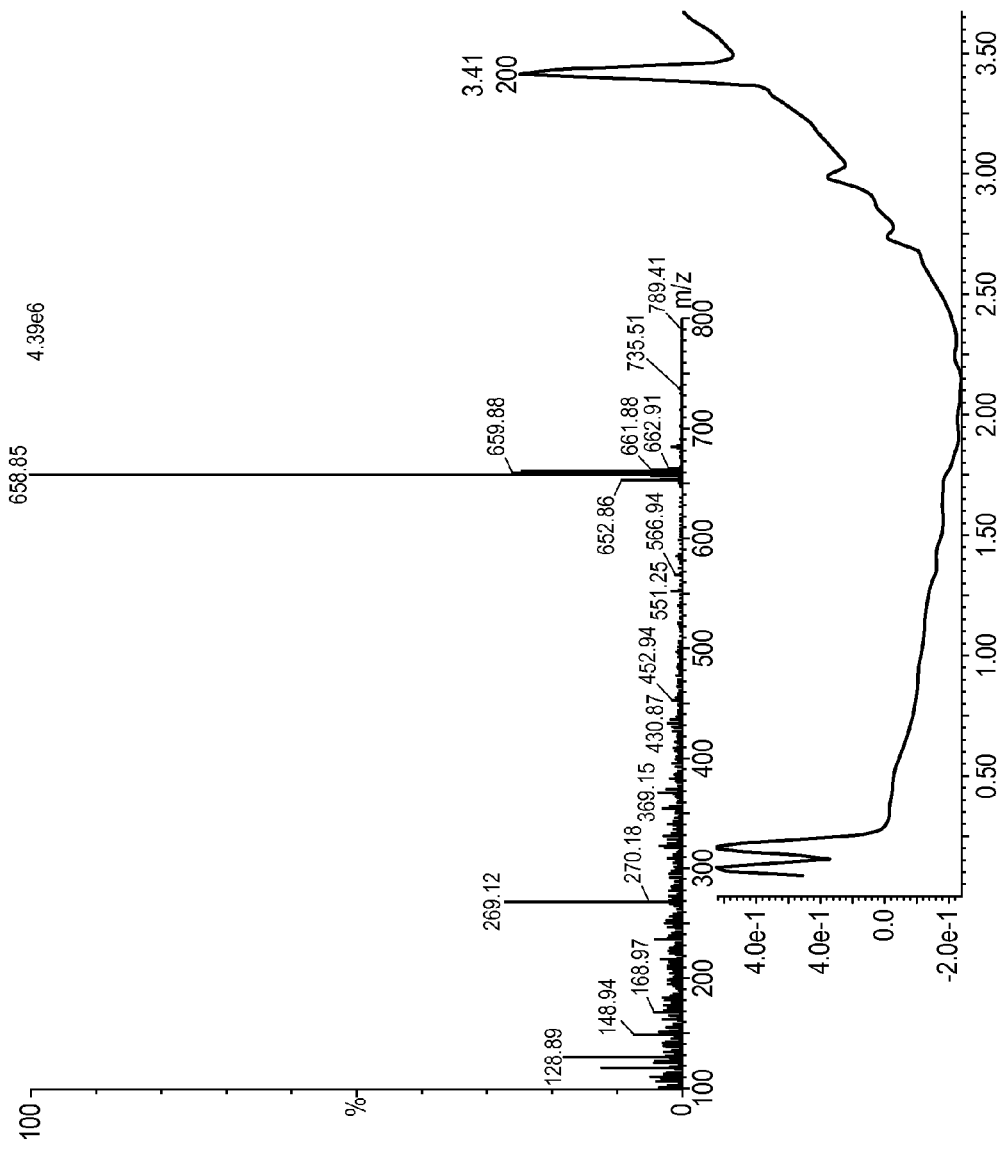
FIG. 4 shows LCMS data for compound 6-[$^3$H$_3$CO]-PSMXB-6.

To a solution of 1 mg (1.56 micromol) PSMXB-4 in 0.5 mL of dry DMF was added ¹/₂₀ equivalent (0.08 micromol) of [$^3H_3$] methyl iodide and the mixture was left to stir over night at room temperature. The crude mixture was then purified by HPLC (Chromasil 100-5-C18 column 250×10 mm) using 80% acetonitrile in 50 mM ammonium acetate at 2.0 mL/min as the eluent ($t_R$ 21.7 minutes). Analytical HPLC-MS of pooled fractions displayed a peak at around 3.5 minutes, with the expected molecular weight (m/z 659) (see FIG. 4), proving the presence of pure (6-[$^3H_3$CO] PSMXB-6) with a very high specific activity.

2,5-di-(1,3,2-Dithiarsolan-2yl)-9(4-[$^{18}F$]fluorophenyl)-6-methoxy-3-fluorone

[$^{18}F$] Fluoride is isolated from the cyclotron target water using a quarternary methyl ammonium resin. [$^{18}F$] Fluoride is eluted with a solution of aqueous potassium carbonate and a phase transfer catalyst (such as kryptofix) in acetonitrile. The eluate is dried and a solution of the appropriate precursor for radiolabeling, e. g. 2-(1,3,2-dithiarsolan-2yl)-9-(4-bromophenyl)-6-methoxy-3-fluorone, 2-(1,3,2-dithiarsolan-2yl)-9(4-iodophenyl)-6-methoxy-3-fluorone, or 2-(1,3,2-dithiarsolan-2yl)-9(4-nitrophenyl)-6-methoxy-3-fluorone is added to the dried residue. The reaction mixture is heated to achieve fluorination and then diluted prior to purification by HPLC. The fraction carrying the product, as determined using on-line radioactivity detection, is collected and the solvents are removed prior to redissolution in a suitable medium, e. g., for i.v. injection, isotonic saline. The product solution is finally sterilised via sterile filtration.

Chemical Structures

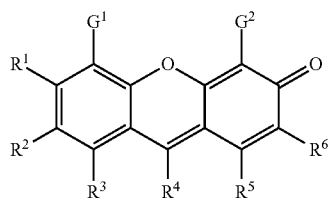

PSMXB-1; $R^2, R^3, R^5, R^6$=H, $G^1, G^2$=H, $R^1$=OH, $R^4$=4-$FC_6H_4$

PSMXB-3; $R^2, R^3, R^5, R^6$=H, $G^1, G^2$=Hg(OCOCF$_3$), $R^1$=OH, $R^4$=4-$FC_6H_4$

PSMXB-4; $R^2, R^3, R^5, R^6$=H, $G^1, G^2$=As(SCH$_2$CH$_2$S), $R^1$=OH, $R^4$=4-$FC_6H_4$

PSMXB-6; $R^2, R^3, R^5, R^6$=H, $G^1, G^2$=As(SCH$_2$CH$_2$S), $R^1$=OMe, $R^4$=4-$FC_6H_4$

Example 2

Binding Studies and Complexes

Binding of the compound PSMXB-6 to Biotin-His-Arg-Trp-Cys-Cys-Pro-Gly-Cys-Cys-Lys-Thr-Phe [SEQ ID NO 2]

Figure 1B:
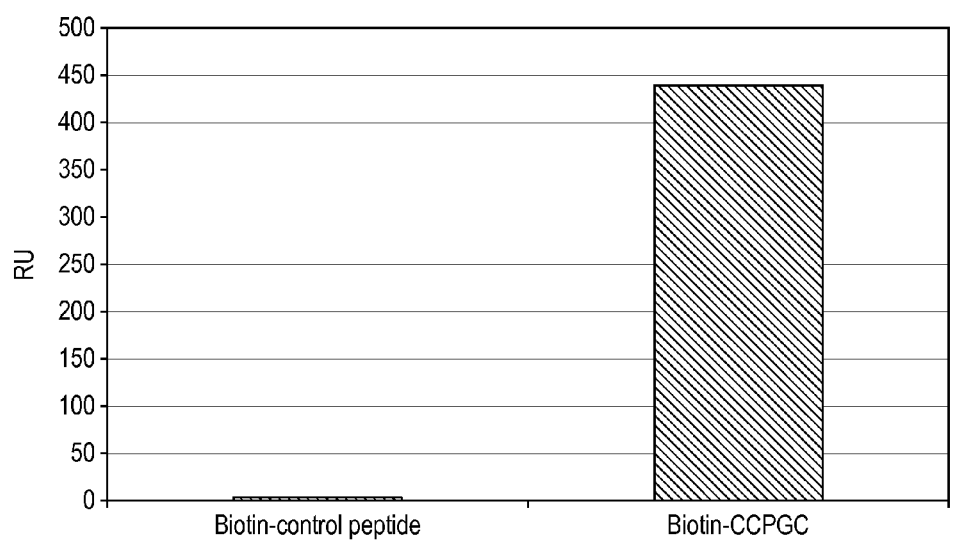
FIG. 1(B) shows a summary of bound PSMXB-6 at the end of the injection phase to N-His-Arg-Trp-Cys-Cys-Pro-Gly-Cys-Cys-Lys-Thr-Phe-C [SEQ ID NO 2] (biotin-CCPGCC [SEQ ID NO 4]) and an unrelated control peptide.

The target peptide sequence N-His-Arg-Trp-Cys-Cys-Pro-Gly-Cys-Cys-Lys-Thr-Phe-C [SEQ ID NO 2] was synthesized and conjugated with biotin at the N-terminal according to a literature procedure (Martin BR, Giepmans BN, Adams SR, Tsien RY. *Nature Biotechnol.* 2005, 223 (10), 1308-14). The biotinylated peptide was immobilized on a sensor chip (Sensor Chip SA BiaCore) by non-covalent capture to streptavidin according to manufacturer instructions. An unrelated peptide with N-terminal biotin was coupled to a reference channel. A solution of 100 μM PSMXB-6 diluted in degassed buffer, 0.01 HEPES pH7.4, 0.15 M NaCl was injected over the sensor surface at 5 microlitres/min for 5 min (Injection arrow, FIG. 1A). 100 microM PSMXB-6 rapidly interacted with the tetracysteine-tagged target sequence His-Arg-Trp-Cys-Cys-Pro-Gly-Cys-Cys-Lys-Thr-Phe [SEQ ID NO 2] reaching a steady state level of about 440 RU (response units) (FIG. 1). FIG. 1A shows the real time interaction of PSMXB-6 with immobilised Biotin-His-Arg-Trp-Cys-Cys-Pro-Gly-Cys-Cys-Lys-Thr [SEQ ID NO 1] using surface plasmon resonance technology (BiaCore 3000). At the end of the injection phase, the sensor surface was washed (Wash arrow FIG. 1A) with 0.01 HEPES pH7.4, 0.15 M NaCl. PSMXB-6 binding was stable during the washing procedure showing a very low dissociation rate of PSMXB-6. No interaction was detected with the unrelated non-tagged peptide N-His-Arg-Trp-Cys-Cys-Pro-Gly-Cys-Cys-Lys-Thr-Phe-C [SEQ ID NO 2] (biotin-CCPGCC [SEQ ID NO 4]) as seen in FIG. 1 B. The steady state level of bound PSMXB-6 corresponds to a 1:1 stoichiometry of binding to the target peptide sequence, as expected. The high association rate and the low dissociation rate of PSMXB-6 binding to N-His-Arg-Trp-Cys-Cys-Pro-Gly-Cys-Cys-Lys-Thr-Phe-C [SEQ ID NO 2] shown in FIG. 1(A) indicates a high affinity interaction.

Binding of the Compound PSMXB-4 and PSMXB-6 to a Tetracysteine-Tagged Peptide

Experiments were performed according to Nature Protocols Vol.3 No.9, 1527-1534, (Adams & Tsien) with minor modifications.

Materials: Peptide (NH2—)FLNCCPGCCMEP(—COOH) [SEQ ID No 6], M.w: 1316.63, supplied by INNOVAGEN, Sweden, MOPS sodium salt FW: 231.2 CAS [71119-22-7], MES sodium salt FW: 164.16 CAS [19767-45-4], and EDT FW:94.2 CAS [540-63-6] were used as received.

HPLC analyses employed a Waters Alliance 2795 LC system, equipped with an XBridge C18 3.0×50 mm 3.5 μm column. The mass detector had polarity ES+/polarity ES-. Solvents, A: 0.1 M NH$_3$ in milliQ water, B: MeOH. Gradient, A: 95% 0.1 min, 0.1-4 min A:95% to B:100%, 4.0-4.6 min B:100%.

The radiodetector employed was a Raytest Star (solid cell). Chromatography with radiodetection was performed using a Kromasil C18, 5μ 250×10 mm column, and an isocratic eluent composed of 35% acetonitrile in 50 mM ammonium acetate, at a flow rate of 2.0 mL/min.

PSMXB-4 Binding

Figure 2:
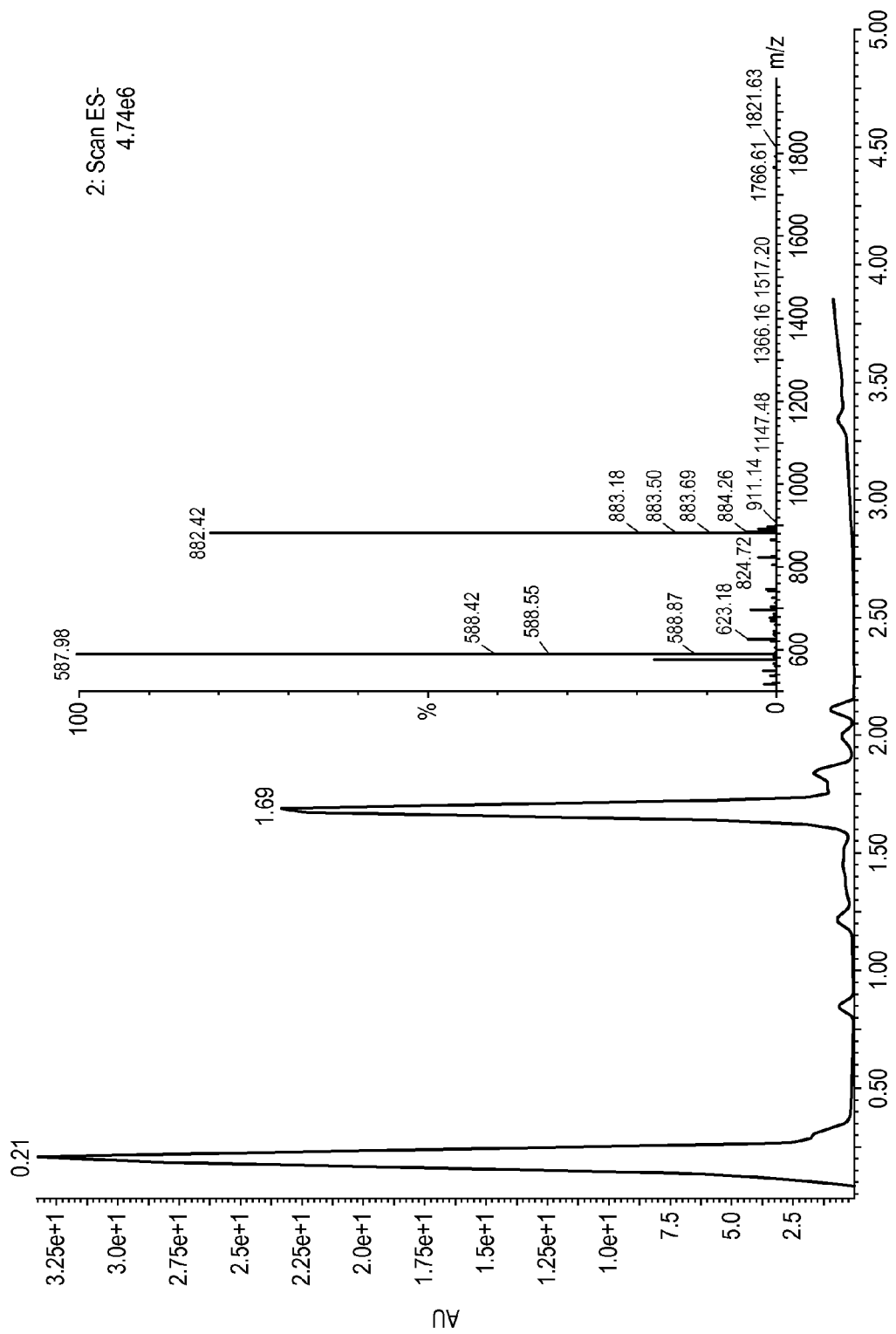
FIG. 2 shows LC-MS data for a complex formed between compound PSMXB-4 and a tetracysteine-tagged peptide.

To 300 μL MOPS 100 mM buffer was added 25 μof freshly prepared 1 M MES$^\#$, and 2.5 μL of freshly prepared 10 mM EDT (in DMSO). To this solution was added 200 μL of 1 mM PSMXB-4 (in DMSO). The mixture was stirred vigorously for one minute before 200 μL of 1 mM peptide (in 50% acetonitrile/water+0.1% TFA) was introduced. The reaction mixture was stirred for 30 minutes. LC-MS analysis showed a mass spectrum consistent with the complex (m/z 882; 588) (see FIG. 2). The mass peaks corresponded to dianionic and trianionic species.

PSMXB-6 Binding

Figure 3:
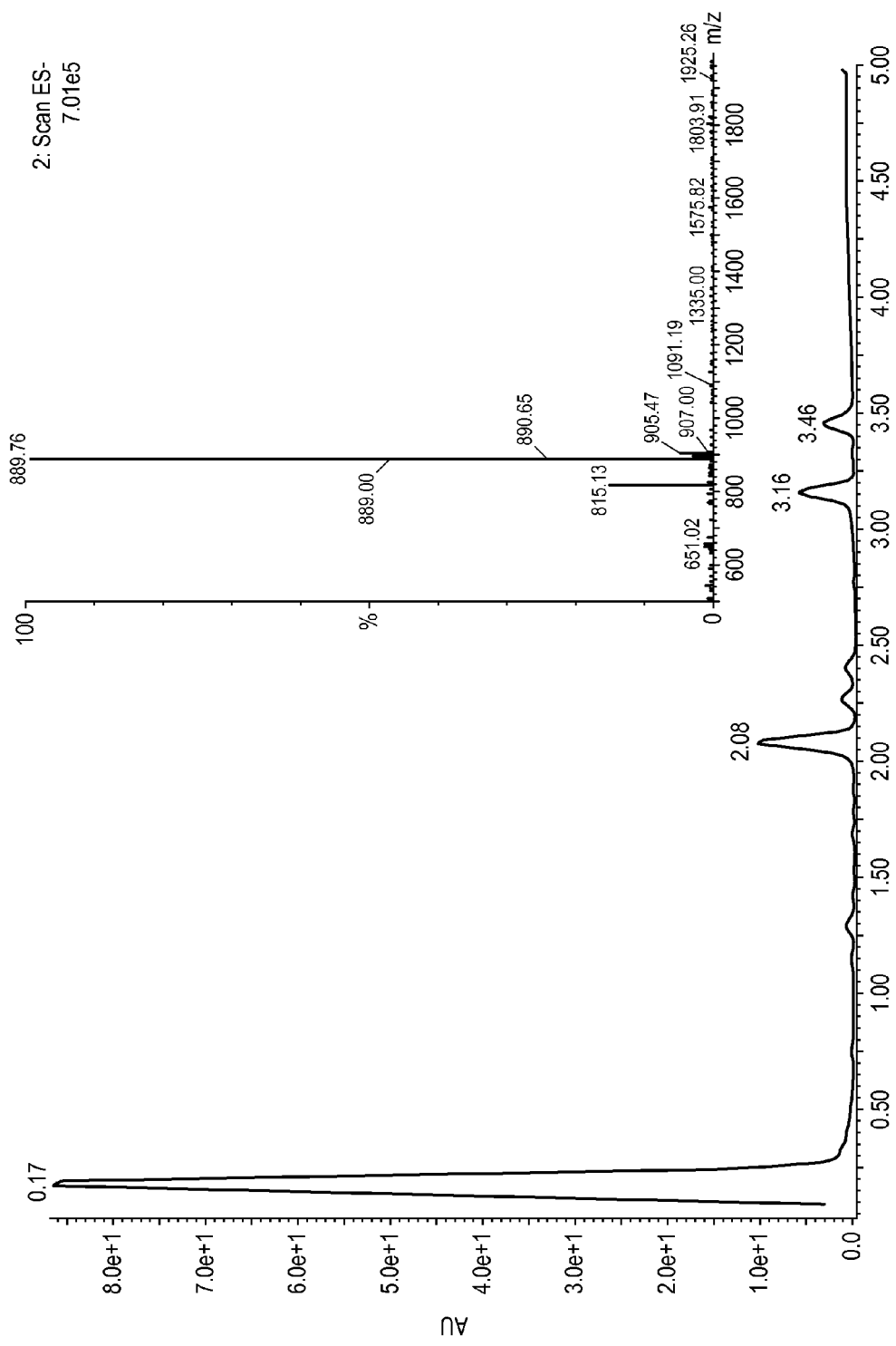
FIG. 3 shows LC-MS data for a complex formed between compound PSMXB-6 and a tetracysteine-tagged peptide.

To 300 μL MOPS 100 mM buffer was added 25 μL of freshly prepared 1 M MES$^\#$, and 2.5 μL of freshly prepared 10 mM EDT (in DMSO). To this solution was added 200 μL of 1 mM PSMXB-6 (in DMSO). The mixture was stirred vigorously for one minute before 200 μL of 1 mM peptide (in 50% acetonitrile/water+0.1% TFA) was introduced. The reaction mixture was stirred for 30 minutes. LC-MS analysis showed a mass spectrum consistent with the complex (m/z 890) (see FIG. 3). The mass peak corresponded to the dianionic species.

It was noted, that the two complexes prepared above were stable in solution at room temperature for more than two weeks, without any signs of decomposition.

Binding of Labeled PSMXB-6

Figure 5A:
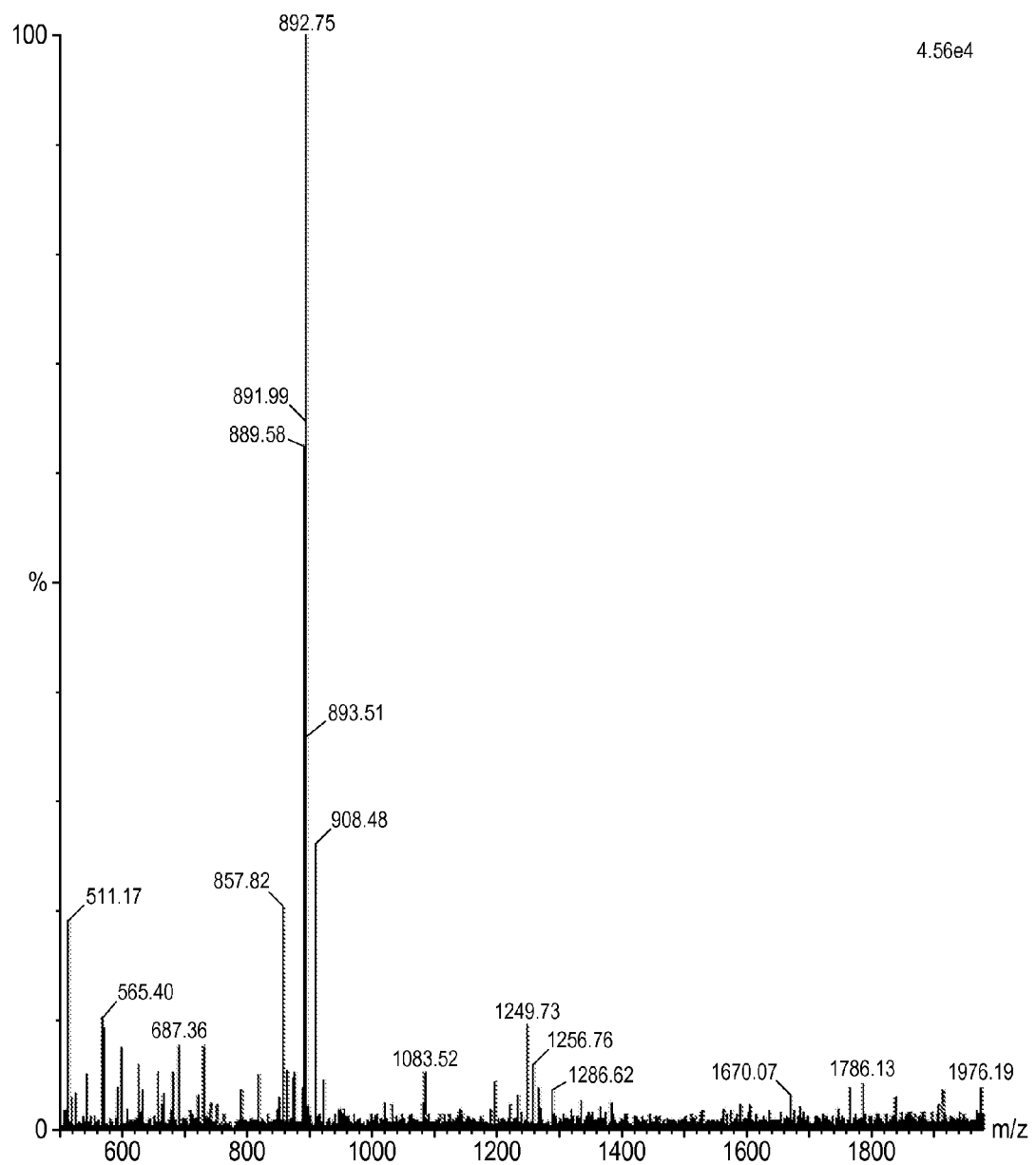
FIGS. 5(A), 5(B) and 5(C) show LCMS and radiodetection data for a complex formed between compound 6-[$^3$H$_3$CO]-PSMXB-6 and a tetracysteine-tagged peptide.
Figure 5B:
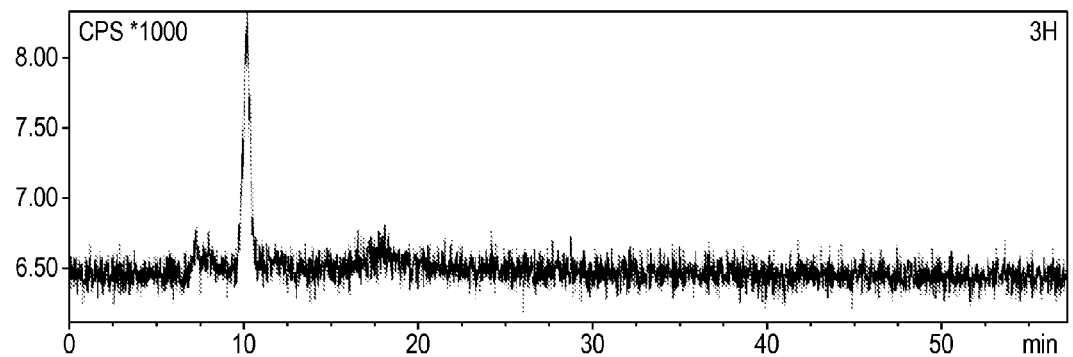
Figure 5C:
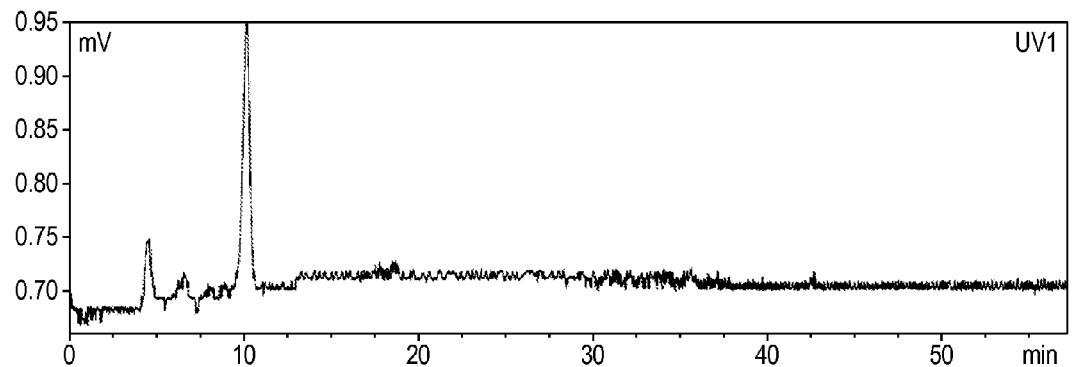

To 250 uL of MOPS 100 mM buffer was added 25 μL of freshly prepared 1 M MES$^\#$, and 2.5 μL of freshly prepared 10 mM EDT (in DMSO). To this solution was added 200 μL of 20 MBq 6-[$^3$H$_3$CO]-PSMXB-6 (in DMSO). The mixture was stirred vigorously for one minute, before 250 μL of 1 mM peptide (in 50% acetonitrile/water+0.1% TFA, 250 ug peptide) was introduced. The reaction mixture is stirred for 10 minutes. LC-MS analysis showed a mass spectrum consistent with complete conversion into the complex (m/z 893). The mass peak corresponded to the dianionic species. When the same complex was injected into an HPLC system equipped with a radiodetector, a peak at about 10 minutes retention time appeared along with multiple impurity peaks eluting earlier. HPLC purification allowed isolation of the pure, tritiated complex. FIGS. 5A, 5B and 5C show analysis via LC-MS, which again revealed a peak at about 2 minutes retention time with the m/z attributable to the dianionic complex (893), and radiodetection, which clearly proves the presence of a single radioactive species with $t_R$ at 10 minutes. Importantly, reanalysis several weeks after the isolation of the complex indicated adequate stability of the radiolabelled species.

Binding of the Compound PSMXB-6 to a Tetracysteine-Tagged Peptide In Vivo

Materials: MSH Peptide (melanin stimulating hormone with CCPGCC tag) NH2— Ac-Ser-Tyr-Ser-Nle-Glu-His-D-Phe-Arg-Trp-Gly-Lys-Pro-Val-Phe-Leu-Asn-Cys-Cys-Pro-Gly-Cys-Cys-Met-Pro-COOH [SEQ ID NO 5], supplied by INNOVAGEN, Sweden, MOPS sodium salt FW: 231.2 CAS [71119-22-7], MES sodium salt FW: 164.16 CAS [19767-45-4], and EDT FW:94.2 CAS [540-63-6].

6-[$^3$H$_3$CO]-PSMXB-6 Binding to MSH-Peptide

Experiments are performed according to Nature Protocols 2008, Vol. 3 No. 9, 1527-1534, with minor modifications. To 300 μL MOPS 100 mM buffer, 25 μL of freshly prepared 1 M MES, and 2.5 μL of freshly prepared 10 mM EDT (in DMSO) are added. To this solution, 200 μL of 10 μM 6-[$^3$H$_3$CO]-PSMXB-6 (in DMSO) are added. The mixture is stirred vigorously for one minute, before 200 μL of 1 mM peptide (in 50% acetonitrile/water+0.1% TFA) is introduced. The reaction mixture is stirred for 30 minutes. LC-MS analysis of the mass peaks is used to identify the 6-[$^3$H$_3$CO]-PSMXB-6-MSH-peptide complex, and semi-preparative HPLC is used for purifying the radiolabelled MSH peptide ([$^3$H]PSMXB-6-MSH-peptide).

Small Animal Ex Vivo Autoradiography of 6-[$^3$H$_3$CO]-PSMXB-6-MSH-Peptide Binding to Melanoma Tumor Cells Experiments are performed according to Journal of Nuclear Medicine, 2007, Vol. 48 No. 6, 987-994, with minor modifications. B16-F10 melanoma tumor cells (ATCC) expressing high levels of melanocortin 1 receptors are inoculated subcutaneously in female C57BL/6 mice. Seven to fourteen days after inoculation, purified 6-[$^3$H$_3$CO]-PSMXB-6-MSH-peptide (100-200 nmol/kg) is intravenously infused via the tail vein over a 30 second period in one group of animals. Blocking experiments are performed by infusing via the tail vein 200 μg of NDP ([Nle$^4$,D-Phe$^7$]μ-MSH followed by 6-[$^3$H$_3$CO]-PSMXB-6-MSH-peptide (100-200 nmol/kg) in another group of B16/F10 inoculated female C57BL/6 mice. Animals are sacrificed at different time points, 1-12h after the injection, and rapidly frozen in a mixture of dry ice and methanol. Whole body autoradiography analysis is performed as described in Curr. Drug. Metab., 2002 Vol. 3 No. 5, 451-462. The data reveals that tumour uptake values of 6-[$^3$H$_3$CO]-PSMXB-6-MSH-peptide are significantly higher than that of surrounding tissues in B16/F10 inoculated C57BL/6 mice. The specific binding component in the tumour tissue is blocked by preinjection of an excess of blocking peptide NDP. This shows that 6-[$^3$H$_3$CO]-PSMXB-6-MSH-peptide can bind to melanocortin 1 receptors in the living mice.

The invention claimed is:

1. A compound of formula I:

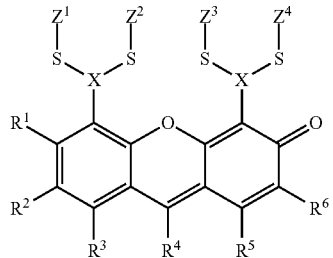

wherein

X is As or P, $Z^1$-$Z^4$ are each independently lower alkyl, or $Z^1$ and $Z^2$ or $Z^3$ and $Z^4$, or both, together form an ethylene or propylene chain, which may optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl);

$R^1$ is selected from the group consisting of hydrogen, halogen, hydroxy, formyl, cyano, —$CONH_2$, —$CONH(C_1$-$C_6$ alkyl), —$CON(C_1$-$C_6$ alkyl)$_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkylamino, mono- or di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkylamino, mono- or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkyl amino, mono- or di- $C_6$-$C_{10}$ arylamino, $C_1$-$C_6$ alkylthio, $C_6$-$C_{10}$ arylthio, halogen, hydroxy, formyl, cyano, —$CONH_2$, —$CONH(C_1$-$C_6$ alkyl), —$CON(C_1$-$C_6$ alkyl)$_2$, and —$NHCO(C_1$-$C_6$ alkyl);

$R^2$, $R^3$, $R^5$ and $R^6$ are each independently selected from the group consisting of hydrogen, halogen, formyl, cyano, —$CONH_2$, —$CONH(C_1$-$C_6$ alkyl), —$CON(C_1$-$C_6$ alkyl)$_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkylamino, di- $C_6$-$C_{10}$arylamino, $C_1$-$C_6$ alkylthio and $C_6$-$C_{10}$ arylthio, wherein said $C_1$-$C_6$ alkyl, $C_6$-$C_{10}$aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl,$C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl); and at least one of $R^1$-$R^6$ comprises an isotope atom.

2. A compound according to claim 1, wherein at least one of $R^1$-$R^6$ comprises a radioactive isotope atom.

3. A compound according to claim 1, wherein X is As.

4. A compound according to claim 1, wherein $Z^1$-$Z^4$ are each independently $C_{1-6}$ alkyl, or $Z^1$ and $Z^2$ or $Z^3$ and $Z^4$, or both, together form an ethylene or propylene chain.

5. A compound according to claim 1, wherein $R^2$ and $R^6$ are each hydrogen; and at least one of $R^1$, $R^3$, $R^4$, and $R^5$ comprises an isotope atom.

6. A compound according to claim 1, wherein $R^2$, $R^3$, $R^5$ and $R^6$ are each hydrogen; and at least one of $R^1$ and $R^4$ comprises an isotope atom.

7. A compound according to claim 1, wherein $R^1$ is selected from the group consisting of: hydroxy, $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-6}$alkoxy, mono- or di- $C_1$-$C_6$ alkyl amino, and cyano; and at least one of $R^1$ and $R^4$ contains at least one radioactive isotope atom.

8. A compound according to claim 1, wherein at least one of $R^1$ and $R^4$ contains at least one radioactive isotope atom.

9. A compound according to claim 1, wherein X is As;

$Z^1$-$Z^4$ are each independently $C_{1-6}$alkyl, or $Z^1$ and $Z^2$ or $Z^3$ and $Z^4$, or both, together form an ethylene or propylene chain;

$R^2$, $R^3$, $R^5$ and $R^6$ are each hydrogen;

$R^1$ is selected from the group consisting of hydroxy, $C_1$-$C_6$ alkoxy, and $C_6$-$C_{10}$ aryloxy, wherein said $C_1$-$C_6$ alkoxy or $C_6$-$C_{10}$ aryloxy may optionally be substituted with up to three substituents independently selected from halogen, $C_{1-6}$ alkyl optionally substituted by one or more halogens, $C_{2-4}$ alkenyl, $C_{2-4}$ alkynyl, $C_{1-3}$ alkoxy, mono- or di- $C_1$-$C_6$ alkyl amino, and cyano;

$R^4$ is $C_6$-$C_{10}$ aryl optionally substituted with up to three substituents independently selected from halogen, $C_{1-6}$alkyl optionally substituted by one or more halogens, $C_{2-4}$ alkenyl, $C_{2-4}$ alkynyl, $C_{1-3}$alkoxy, mono- or di- $C_1$-$C_6$ alkyl amino, and cyano; and at least one of $R^1$ and $R^4$ comprises a radioactive isotope atom.

10. A compound according to claim 1, wherein:

a) $R^1$ is hydroxy or methoxy; and either $R^4$ is optionally substituted phenyl containing at least one $^{11}$C, or $^{14}$C, wherein said phenyl may optionally be substituted with up to three substituents independently selected from halogen, $C_{1-6}$alkyl optionally substituted by one or more halogens, $C_{2-4}$ alkenyl, $C_{2-4}$ alkynyl, $C_{1-3}$alkoxy, mono- or di- $C_1$-$C_6$ alkyl amino, and cyano, or $R^4$ is phenyl substituted with one or more of NHC$^3$H$_3$, NH$^{11}$CH$_3$, NH$^{14}$CH$_3$, NCH$_3$(C$^3$H$_3$), NCH$_3$($^{11}$CH$_3$), NCH$_3$($^{14}$CH$_3$), $^{76}$Br, $^{123}$I, $^{125}$I, $^{131}$I, $^3$H, or $^{18}$F, or wherein:

b) $R^1$ is selected from the group consisting of C$^3$H$_3$O, $^{11}$CH$_3$O, and $^{14}$CH$_3$O; and $R^4$ is phenyl optionally substituted with up to three substituents independently selected from halogen, $C_{1-6}$alkyl optionally substituted by one or more halogens, $C_{2-4}$ alkenyl, $C_{2-4}$ alkynyl, $C_{1-3}$alkoxy, mono- or di- $C_1$-$C_6$ alkyl amino, and cyano.

11. A compound according to claim 1, wherein:

$Z^1$ and $Z^2$, and $Z^3$ and $Z^4$, respectively, together represent ethylene, $R^2$, $R^3$, $R^5$, and $R^6$ are hydrogen, and a) $R^1$ is methoxy, and either $R^4$ is optionally substituted phenyl containing at least one $^{11}$C, or $^{14}$C, wherein said phenyl may optionally be substituted with up to three substituents independently selected from halogen, $C_{1-6}$alkyl optionally substituted by one or more halogens, $C_{2-4}$ alkenyl, $C_{2-4}$ alkynyl, $C_{1-3}$alkoxy, mono- or di- $C_1$-$C_6$ alkyl amino, and cyano, or $R^4$ is phenyl substituted with one or more of NHC$^3$H$_3$, NH$^{11}$CH$_3$, NH$^{14}$CH$_3$, NCH$_3$(C$^3$H$_3$), NCH$_3$($_{11}$CH$_3$), NCH$_3$($^{14}$CH$_3$), $^{76}$Br, $^{123}$I, $^{123}$I, $^{125}$I, $^{131}$I, $^3$H, or $^{18}$F;

or b) $R^1$ is selected from the group consisting of C$^3$H$_3$O, $^{11}$CH$_3$O, and $^{14}$CH$_3$O; and $R^4$ is 4-fluorophenyl.

12. A method for synthesizing a compound of formula I as defined in claim 1, comprising the steps of a1) reacting a compound of formula IIA

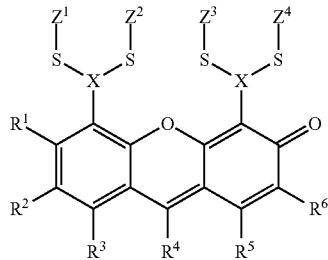

wherein:

X is As or P;

$Z^1$-$Z^4$ are independently lower alkyl, or $Z^1$ and $Z^2$ or $Z^3$ and $Z^4$, or both, together form an ethylene or propylene chain, which alkyl, ethylene or propylene chain may optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —CONH$_2$, —CONH($C_1$-$C_6$ alkyl), —CON($C_1$-$C_6$ alkyl)$_2$, and —NHCO($C_1$-$C_6$ alkyl);

$R^1$ is hydroxy;

$R^4$ is $C_6$-$C_{10}$ aryl optionally substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono- or di- $C_6$-$C_{10}$ arylamino, $C_1$-$C_6$ alkylthio, $C_6$-$C_{10}$ arylthio, halogen, hydroxy, formyl, cyano, and —NHCO($C_1$-$C_6$ alkyl); and $R^2$, $R^3$, $R^5$ and $R^6$ are each independently selected from the group consisting of hydrogen, halogen, formyl, cyano, —CONH$_2$, —CONH($C_1$-$C_6$ alkyl), —CON($C_1$-$C_6$ alkyl)$_2$, —NHCO($C_1$-$C_6$ alkyl), $C_1$-$C_6$alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$alkylthio, $C_6$-$C_{10}$ arylthio, halogen, formyl, cyano, —CONH$_2$, —CONH($C_1$-$C_6$ alkyl), —CON($C_1$-$C_6$ alkyl)$_2$, and —NHCO($C_1$-$C_6$ alkyl);

$R^2$, $R^3$, $R^5$ and $R^6$ are each independently selected from the group consisting of hydrogen, halogen, formyl, cyano, —CONH$_2$, —CONH($C_1$-$C_6$ alkyl), —CON($C_1$-$C_6$ alkyl)$_2$, —NHCO($C_1$-$C_6$ alkyl), $C_1$-$C_6$alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl);

with a $C_1$-$C_6$alkyl group which comprises a leaving group and at least one isotope atom;

or a2) reacting a compound of formula IIIA

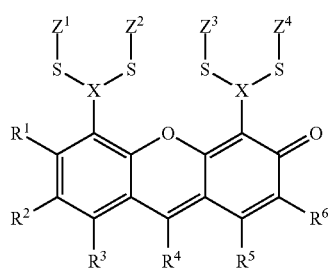

IIIA wherein:

X is As or P;

$Z^1$-$Z^4$ are independently lower alkyl, or $Z^1$ and $Z^2$ or $Z^3$ and $Z^4$, or both, together form an ethylene or propylene chain, which alkyl, ethylene or propylene chain may optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl); and $R^1$ is selected from the group consisting of hydrogen, halogen, hydroxy, formyl, cyano, —$CONH_2$, —$CONH(C_1$-$C_6$ alkyl), —$CON(C_1$-$C_6$ alkyl)$_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkylamino, mono- or di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkylamino, mono- or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl,$C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkyl amino, mono- or di- $C_6$-$C_{10}$ arylamino, $C_1$-$C_6$ alkylthio, $C_6$-$C_{10}$ arylthio, halogen, hydroxy, formyl, cyano, —$CONH_2$, —$CONH(C_1$-$C_6$ alkyl), —$CON(C_1$—$C_6$ alkyl)$_2$, and —$NHCO(C_1$-$C_6$ alkyl);

$R^4$ is phenyl substituted with a leaving group, wherein the phenyl is not substituted with —COOH; and $R^2$,$R^3$, $R^5$ and $R^6$ are independently selected from the group consisting of hydrogen, halogen, formyl, cyano, —$CONH_2$, —$CONH(C_1$-$C_6$ alkyl), —$CON(C_1$-$C_6$ alkyl)$_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkylamino, di- $C_6$-$C_{10}$arylamino, $C_1$-$C_6$ alkylthio and $C_6$-$C_{10}$ arylthio, wherein said $C_1$-$C_6$ alkyl, $C_6$-$C_{10}$aryl, $C_6$-$C_{10}$ heteroaryl, $C_1$-$C_6$ acyl, $C_6$-$C_{10}$ aroyl, $_1$-$C_6$ alkoxy, $C_6$-$C_{10}$ aryloxy, di- $C_1$-$C_6$ alkylamino, di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$alkylthio, $C_6$-$C_{10}$ arylthio, halogen, formyl, cyano, —$CONH_2$, —$CONH(C_1$-$C_6$ alkyl), —$CON(C_1$-$C_6$ alkyl)$_2$, and —$NHCO(C_1$-$C_6$ alkyl);

with an isotopic fluorine reagent;

and, optionally b. purifying the so obtained compound of formula I by chromatography, and, optionally c. dissolving or diluting the so purified compound of formula I with a solvent.

13. A compound of formula IIA or formula IIIA as defined in claim 12.

14. A method for visualising a tetracysteine-tagged analyte molecule comprising contacting said tetracysteine-tagged analyte molecule with a compound of formula I as defined in claim 1.

15. The method according to claim 14, wherein the tetracysteine-tagged analyte molecule comprises at least one amino acid sequence of the form -Cys-Cys-$X_{aa}$-$X_{aa}$-Cys-Cys-, wherein each $X_{aa}$ represents a non-cysteine amino acid residue [SEQ ID NO 4].

16. The method according to claim 14, wherein the compound of formula I is visualised by in vitro autoradiography, in vivo PET, in vivo SPECT or in vivo MRI.

17. The method according to claim 14, wherein the analyte molecule is an oligopeptide, a protein, a glycoprotein, or an antibody.

18. The method according to claim 14, wherein the compound of formula I and the tetracysteine-tagged analyte molecule are pre-mixed prior to administration into the matrix where visualisation is desired.

19. The method according to claim 14, wherein the method comprises:

a) contacting a first sample of said tetracysteine-tagged analyte molecule with a first compound of formula I to produce a first tetracysteine-tagged analyte molecule; and b) contacting a second sample of said tetracystein-tagged analyte molecule with a second compound of formula I to produce a second tetracysteine-tagged analyte molecule;

wherein said first and second compounds of formula I differ only in that they comprise a different isotope atom, and wherein said first and second tetracysteine-tagged analyte molecules are visualized by different techniques.

20. A complex between a compound of formula I, as defined in claim 1, and a tetra-cysteine tagged molecule.

21. A complex as claimed in claim 20, wherein the tetra-cysteine tagged molecule comprises at least one sequence of the form -Cys-Cys-$X_{aa}$-$X_{aa}$-Cys-Cys-, wherein each $X_{aa}$ represents a non-cysteine amino acid residue [SEQ ID NO 4].

22. A kit for visualising an analyte molecule, comprising a compound of formula I, as defined in claim 1.

23. A kit for visualising an analyte molecule, comprising a suitable precursor compound of formula IIA or IIIA, as defined in claim 13.

24. A kit comprising a first compound of formula I as defined in claim 1, and a second compound of formula I as defined in claim 1, wherein said first and second compounds of formula I differ only in that they comprise a different isotope atom.

25. A kit comprising:
a first complex between a first compound of formula I, as defined in claim 1, and a first sample of a tetra-cysteine tagged molecule; and
a second complex between a second compound of formula I as defined in claim 1 and a second sample of the tetra-cysteine tagged molecule, wherein said first and second compounds of formula I differ only in that they comprise a different isotope atom.

26. The kit according to claim 22, wherein the analyte molecule is a tetracysteine-tagged analyte molecule, for example an oligopeptide, a protein, a glycoprotein, or an antibody.

27. The complex according to claim 20, wherein the analyte molecule is a tetracysteine-tagged analyte molecule, for example an oligopeptide, a protein, a glycoprotein, or an antibody.

28. A method for the treatment or prophylaxis of melanoma in a mammal, which comprises administering to the mammal a therapeutically effective amount of a compound as claimed in claim 1, wherein at least one of $R^1$-$R^6$ comprises a radioactive isotope atom.

29. A method for the treatment or prophylaxis of melanoma in a mammal, which comprises administering to the mammal a therapeutically effective amount of a complex as claimed in claim 20, wherein at least one of $R^1$-$R^6$ comprises a radioactive isotope atom.

30. A method of visualizing an analyte molecule, comprising:
Administering to a mammal a therapeutically effective amount of a complex between a tetra-cysteine tagged analyte molecule and a compound of formula I:

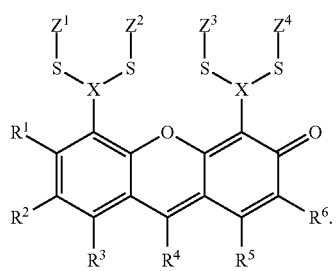

wherein
X is As or P,
$Z^1$-$Z^4$ are each independently lower alkyl, or $Z^1$ and $Z^2$ or $Z^3$ and $Z^4$, or both, together form an ethylene or propylene chain, which may optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$ alkyl$)_2$ and —$NHCO(C_1$-$C_6$ alkyl);

$R^1$ is selected from the group consisting of hydrogen, halogen, hydroxy, formyl, cyano, —$CONH_2$, —$CONH(C_1$-$C_6$ alkyl), —$CON(C_1$-$C_6$ alkyl$)_2$, —$NHCO(C_1$-$C_6$ alkyl), $C_1$-$C_6$ alkyl optionally substituted by one or more halogens, $C_2$-$C_6$ alkenyl, $C_2$-$C_4$ alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkylamino, mono- or di- $C_6$-$C_{10}$ arylamino, $C_1$-$C_6$ alkylthio and $C_6$-$C_{10}$ arylthio, wherein said $C_1$-$C_6$ alkyl, $C_6$-$C_{10}$ aryl, $C_6$-$C_{10}$ heteroaryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkylamino, mono- or di- $C_6$-$C_{10}$ arylamino, $C_1$-$C_6$ alkylthio and $C_6$-$C_{10}$ arylthio may each optionally be substituted by one or more substituents independently selected from the group consisting of $C_1$-$C_6$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono- or di- $C_1$-$C_6$ alkyl amino, mono- or di- $C_6$-$C_{10}$ arylamino, $C_1$-$C_6$ alkylthio, $C_6$-$C_{10}$ arylthio, halogen, hydroxy, formyl, cyano, —$CONH_2$, —$CONH(C_1$-$C_6$alkyl), —$CON(C_1$-$C_6$ alkyl$)_2$, and —$NHCO(C_1$-$C_6$ alkyl); $R^4$ is $C_6$-$C_{10}$ aryl optionally substituted by one or more substituents independently selected from the group consisting of $C_{1-6}$ alkyl optionally substituted by one or more halogens, $C_2$-$C_6$ alkenyl, $C_2$-$C_4$ alkynyl, $C_6$-$C_{10}$ aryl, $C_1$-$C_6$ acyl, $C_6$-$C_{10}$ aroyl, $C_1$-$C_6$ alkoxy, $C_6$-$C_{10}$ aryloxy, mono- or di- $C_6$-$C_{10}$ arylamino, $C_1$-$C_6$ alkylthio, $C_6$-$C_{10}$ arylthio, halogen, hydroxy, formyl, cyano and —$NHCO(C_1$-$C_6$ alkyl);

$R^2$, $R^3$, $R^5$ and $R^6$ are each independently selected from the group consisting of hydrogen, halogen, formyl, cyano, —$CONH_2$, —$CONH(C_1$-$C_6$ alkyl), —$CON(C_1$-$C_6$ alkyl$)_2$, —$NHCO(C_1$-$C_6$ alkyl), $C_1$-$C_6$alkyl optionally substituted by one or more halogens, $C_2$-$C_6$ alkenyl, $C_2$-$C_4$alkynyl, $C_6$-$C_{10}$ aryl, $C_6$-$C_{10}$ heteroaryl, $C_1$-$C_6$ acyl, $C_6$-$C_{10}$ aroyl, $C_1$-$C_6$alkoxy, $C_6$-$C_{10}$ aryloxy, di- $C_1$-$C_6$alkylamino, di- $C_6$-$C_{10}$ arylamino, $C_1$-$C_6$alkylthio and $C_6$-$C_{10}$ arylthio, wherein said $C_1$-$C_6$alkyl, $C_6$-$C_{10}$aryl, $C_6$-$C_{10}$ heteroaryl, $C_1$-$C_6$acyl, $C_6$-$C_{10}$ aroyl, $C_1$-$C_6$alkoxy, $C_6$-$C_{10}$ aryloxy, di- $C_1$-$C_6$alkylamino, di- $C_6$-$C_{10}$ arylamino, $C_1$-$C_6$alkylthio and $C_6$-$C_{10}$ arylthio may each optionally be substituted by one or more substituents independently selected from the group consisting of $C_1$-$C_6$alkyl optionally substituted by one or more halogens, $C_2$-$C_6$alkenyl, $C_2$-$C_4$alkynyl,$C_6$-$C_{10}$ aryl, $C_1$-$C_6$acyl, $C_6$-$C_{10}$ aroyl, $C_1$-$C_6$ alkoxy, $C_6$-$C_{10}$ aryloxy, di- $C_1$-$C_6$ alkyl amino, di- $C_6$-$C_{10}$ arylamino, $C_1$-$C_6$ alkylthio, $C_6$-$C_{10}$ arylthio, halogen, formyl, cyano, —$CONH_2$, —$CONH(C_1$-$C_6$ alkyl), —$CON(C_1$-$C_6$alkyl$)_2$, and —$NHCO(C_1$-$C_6$ alkyl); and at least one of $R^1$-$R^6$ comprises an isotope atom, wherein the analyte molecule is selected from: an oligopeptide, a protein, a glycoprotein, and an antibody.

31. A compound as claimed in claim 1, wherein at least one of $R^1$-$R^6$ comprises a radioactive isotope atom, for use as a medicament.

32. A complex as claimed in claim 20, wherein at least one of $R^1$-$R^6$ comprises a radioactive isotope atom, for use as a medicament.

33. A complex as claimed in claim 32 for use in the treatment or prophylaxis of melanoma.

34. A pharmaceutical composition which comprises a compound as claimed in claim 1, wherein at least one of $R^1$-$R^6$ comprises a radioactive isotope atom, together with a pharmaceutically acceptable carrier.

35. A pharmaceutical composition which comprises a complex as claimed in claim 20, wherein at least one of $R^1$-$R^6$ comprises a radioactive isotope atom, together with a pharmaceutically acceptable carrier.

* * * * *

SEQUENCE LISTING

```
<160> NUMBER OF SEQ ID NOS: 6

<210> SEQ ID NO 1
<211> LENGTH: 11
<212> TYPE: PRT
<213> ORGANISM: artificial sequence
<220> FEATURE:
<223> OTHER INFORMATION: tetracysteine-containing tagging sequence
      derived from human thought

<400> SEQUENCE: 1

His Arg Trp Cys Cys Pro Gly Cys Cys Lys Thr
1               5                   10

<210> SEQ ID NO 2
<211> LENGTH: 12
<212> TYPE: PRT
<213> ORGANISM: artificial sequence
<220> FEATURE:
<223> OTHER INFORMATION: tetracysteine-containing tagging sequence
      derived from human thought

<400> SEQUENCE: 2

His Arg Trp Cys Cys Pro Gly Cys Cys Lys Thr Phe
1               5                   10

<210> SEQ ID NO 3
```

```
<211> LENGTH: 9
<212> TYPE: PRT
<213> ORGANISM: artificial sequence
<220> FEATURE:
<223> OTHER INFORMATION: tetracysteine-containing tagging sequence
      derived from human thought
<220> FEATURE:
<221> NAME/KEY: MISC_FEATURE
<222> LOCATION: (3)..(3)
<223> OTHER INFORMATION: Xaa at positions 3 may be any non-cysteine
      amino acid residue.
<220> FEATURE:
<221> NAME/KEY: MISC_FEATURE
<222> LOCATION: (4)..(4)
<223> OTHER INFORMATION: Xaa at position 4 may be any non-cysteine amino
      acid residue or may be absent.
<220> FEATURE:
<221> NAME/KEY: MISC_FEATURE
<222> LOCATION: (5)..(5)
<223> OTHER INFORMATION: Xaa at position 5 may be any non-cysteine amino
      acid residue or may be absent.
<220> FEATURE:
<221> NAME/KEY: MISC_FEATURE
<222> LOCATION: (6)..(6)
<223> OTHER INFORMATION: Xaa at position 6 may be any non-cysteine amino
      acid residue or may be absent.
<220> FEATURE:
<221> NAME/KEY: MISC_FEATURE
<222> LOCATION: (7)..(7)
<223> OTHER INFORMATION: Xaa at position 7 may be any non-cysteine amino
      acid residue or may be absent.

<400> SEQUENCE: 3

Cys Cys Xaa Xaa Xaa Xaa Xaa Cys Cys
1               5

<210> SEQ ID NO 4
<211> LENGTH: 6
<212> TYPE: PRT
<213> ORGANISM: artificial sequence
<220> FEATURE:
<223> OTHER INFORMATION: tetracysteine-containing tagging sequence
      derived from human thought

<400> SEQUENCE: 4

Cys Cys Pro Gly Cys Cys
1               5

<210> SEQ ID NO 5
<211> LENGTH: 24
<212> TYPE: PRT
<213> ORGANISM: artificial sequence
<220> FEATURE:
<223> OTHER INFORMATION: synthetic construct of melanin stimulating
      hormone with a tetracysteine-containing tagging sequence derived
      from human thought
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MISC_FEATURE
<222> LOCATION: (7)..(7)
<223> OTHER INFORMATION: Xaa is D-phenylalanine

<400> SEQUENCE: 5

Ser Tyr Ser Xaa Glu His Xaa Arg Trp Gly Lys Pro Val Phe Leu Asn
1               5                   10                  15

Cys Cys Pro Gly Cys Cys Met Pro
```

```
<210> SEQ ID NO 6
<211> LENGTH: 12
<212> TYPE: PRT
<213> ORGANISM: artificial sequence
<220> FEATURE:
<223> OTHER INFORMATION: tetracysteine-containing tagging sequence
      derived from human thought

<400> SEQUENCE: 6

Phe Leu Asn Cys Cys Pro Gly Cys Cys Met Glu Pro
1               5                   10
```